(12) United States Patent
Bell et al.

(10) Patent No.: US 6,537,812 B1
(45) Date of Patent: Mar. 25, 2003

(54) METHODS FOR THE PRODUCTION OF TCRγδ+ T CELLS

(75) Inventors: David Nicholson Bell, Brampton (CA); Danna Lynn Skea, Mississauga (CA); Phyllis Robin Hedge, Cambridge (CA)

(73) Assignee: Hemosol Inc., Mississauga (CA)

( * ) Notice: Subject to any disclaimer, the term of this patent is extended or adjusted under 35 U.S.C. 154(b) by 0 days.

(21) Appl. No.: 09/807,987

(22) PCT Filed: Nov. 4, 1999

(86) PCT No.: PCT/CA99/01024
§ 371 (c)(1),
(2), (4) Date: Jul. 30, 2001

(87) PCT Pub. No.: WO00/26347
PCT Pub. Date: May 11, 2000

Related U.S. Application Data
(60) Provisional application No. 60/107,006, filed on Nov. 4, 1998.

(51) Int. Cl.[7] .............................. C12N 5/00; C12N 5/02
(52) U.S. Cl. ......................... 435/405; 435/325; 435/41; 435/373; 435/383; 435/384
(58) Field of Search .................................... 435/373, 325, 435/375, 377, 384; 514/41, 405, 102

(56) References Cited

U.S. PATENT DOCUMENTS
| | | | |
|---|---|---|---|
| 5,639,653 A | | 6/1997 | Bloom et al. |
| 5,877,299 A | * | 3/1999 | Thomas et al. ............. 530/413 |
| 6,194,207 B1 | * | 2/2001 | Bell et al. .................... 435/377 |

FOREIGN PATENT DOCUMENTS
| | | |
|---|---|---|
| WO | WO 9819167 | 5/1998 |
| WO | WO 9833891 | 8/1998 |
| WO | WO 99/46365 | 9/1999 |

OTHER PUBLICATIONS

CE Roark et al., Journal of Immunology, "TCR Junctions Reveal Differences in Heat Shock Protein–60–Reactive Cells in Liver and Spleen," Jun. 1993, Vol. 150, No. 11, pp. 4867–4875.*
Barcena A., et al: "A Role For Interleukin 4 In The Differentiation Of Mature T Cell Receptor γδ+ Cells From Human Intrathymic T Cell Precursors.", Journal of Experimental Medicine, (Aug. 1, 1990) 172 (2) 439–46., XP000876697 p. 441, col. 2, paragraphs 1, 3; table 1.
Bensussan, A. et al: "Human Cd3 γδ+ Activated Lymphocytes Exhibit Killer Activity in Vitro Against Autologous Leukemic Cells", Nouv Rev Fr Hematol 31:129, 1989.
Boismenu, R., Havran, W.L.: "An Innate View Of γδ T Cells", Curr Op Immunol 9:57, 1997.
Bukowski, J.F. et al: "Recognition And Destruction Of Virus–Infected Cells By Human γδ CTL", J. Immunol 153:5133, 1994.
Choudhary, A. et al: "Selective Lysis Of Autologous Tumor Cells By Recurrent γδ Tumor–Infiltrating Lymphocytes From Renal Carcinoma", J Immunol 154:3932, 1995.
Constant, P. et al.: "Stimulation Of Human γδ T Cells By Nonpeptidic Mycobacterial Ligands", Science 264:267, 1994.
Elloso, M.M. et al: "Human γδ T Cell Subset–Proliferative Response To Malarial Antigen In Vitro Depends On CD4+ Cells Or Cytokines That Signal Through Components Of The Il–2R", J. Immunol. 157:2096, 1996.
Garcia, V.E. et al.: "IL–15 Enhances The Response Of Human γδ T Cells To Non–Peptide Microbial Antigens", J. Immunol. 160:4322, 1998.
Jahn, B. et al: "Bone Marrow–Derived T–Cell Clones Obtained From Untreated Acute Myeloocytic Leukemia Exhibit Blast Directed Autologous Cytotoxicity", Leuk Res 19:73, 1995.
Kaur, I. et al: "Human Peripheral γδ T Cells Recognize hsp60 Molecules on Daudi Burkitt's Lymphoma Cells", J. Immunol. 150:2046, 1993.
Kitayama, J. et al: "functional analysis of TCR γδ+ I Cells In Tumour–Infiltrating Lymphocytes (TIL) Of Human Pancreatic Cancer", Clin Exp Immunol 93:442, 1993.
Lamb Jr., L.S. et al: "Increased Frequency Of TCR γδ + Cells In Disease–Free Survivors Following T Cell–Depleted, Partially Mismatched, Related Donor Bone Marrow Transplantation For Leukemia", J Hematother, 5:503, 1996.
Lang, F. et al: "Early Activation Of Human Vγ9Vδ2 T Cell Broad Cytotoxicity And TNF Production By Nonpeptidic Mycobacterial Ligands", The Journal of Immunology 5987, 1995.
Orsini, D.L.M. et al: "A Subset Of Vδ1+ T Cells Proliferates In Response To Epstein–Barr Virus–Transformed B Cell Lines In Vitro", Scand. J. Immunol. 38:335, 1993.
Penninger, J. M. et al: "Spontaneous Resistance To Acute T–Cell Leukaemias In TCRVδ1.1Jγ4Cγ4 Transgenic Mice", Nature 375:241, 1995.

(List continued on next page.)

*Primary Examiner*—Jeffrey Fredman
*Assistant Examiner*—Jon Eric Angell
(74) *Attorney, Agent, or Firm*—Bereskin & Parr; Micheline Gravelle

(57) ABSTRACT

The method for obtaining and expanding TcRγδ+ T cells in culture is described. The method involves: 1) culturing cells from a sample containing TcRγδ+ T cells or precursors thereof in a first culture medium comprising a T cell mitogen and at least two cytokines and 2) culturing the cells obtained in step 1) in a second culture medium comprising at least two cytolines. Preferably, the method comprises 1) culturing the cells in a first culture medium comprising (a) a T cell mitogen, (b) interleukin-2 and (c) interleukin-4, and 2) culturing the cells obtained in step 1) in a second culture medium comprising (i) interleukin-2 and (ii) interleukin-4 to obtain TcRγδ+ T cells. The TcRγδ+ T cells obtained by the method can be used in a variety of experimental, therapeutic and commercial applications.

31 Claims, 18 Drawing Sheets

OTHER PUBLICATIONS

Suzuki, Y. et al.: "Enhancing Effect Of Tumor Necrosis Factor (TNF)–α, but not IFN–γ, On The Tumor –Specific Cytotoxicity Of γδT Cells From Glioblastoma Patients", Cancer Lett. 140:161, 1999.

Wallace, M. et al.: "Gamma/delta T Lymphocytes In Viral Infections", J. Leuk Biol 58:277, 1995.

Yamaguchi, T. et. al.:"A Simple Method for the Propagation and Purification of γδT Cells From the Peripheral Blood of Glioblastoma Patients Using Solid–Phase anti CD3 Antibody and Soluble IL–2", Journal of Immunological Mehods 205 (1997) 19–28.

Yu, S. et. al.: "Expansion and Immunological Study of Human Tumor Infiltrating Gamma/Delta T Lymphocytes in vitro", Int Arch Allergy Immunol 1999;119:31–37.

Zocchi, M. R. et. al.: "Selective Lysis of the Autologous Tumor by δTCSI$^+$ γ/δ$^+$ Tumor–Infiltrating Lymphocytes from Human Lung Carcinomas", Eur. J. Immunol. 1990, 20:2685–2689.

Skea, D. et. al.: "The Selective Expansion of Functional T Cell Subsets", Journal of Hematotherapy & Stem–Cell Research 8:525–538 (1999).

Skea, D. et. al.: "Large Ex Vivo Expansion of Human Umbilical Cord Blood CD4$^+$ and CD8$^+$ T Cells," Journal of Hematotherapy 8:129–139 (1999).

* cited by examiner

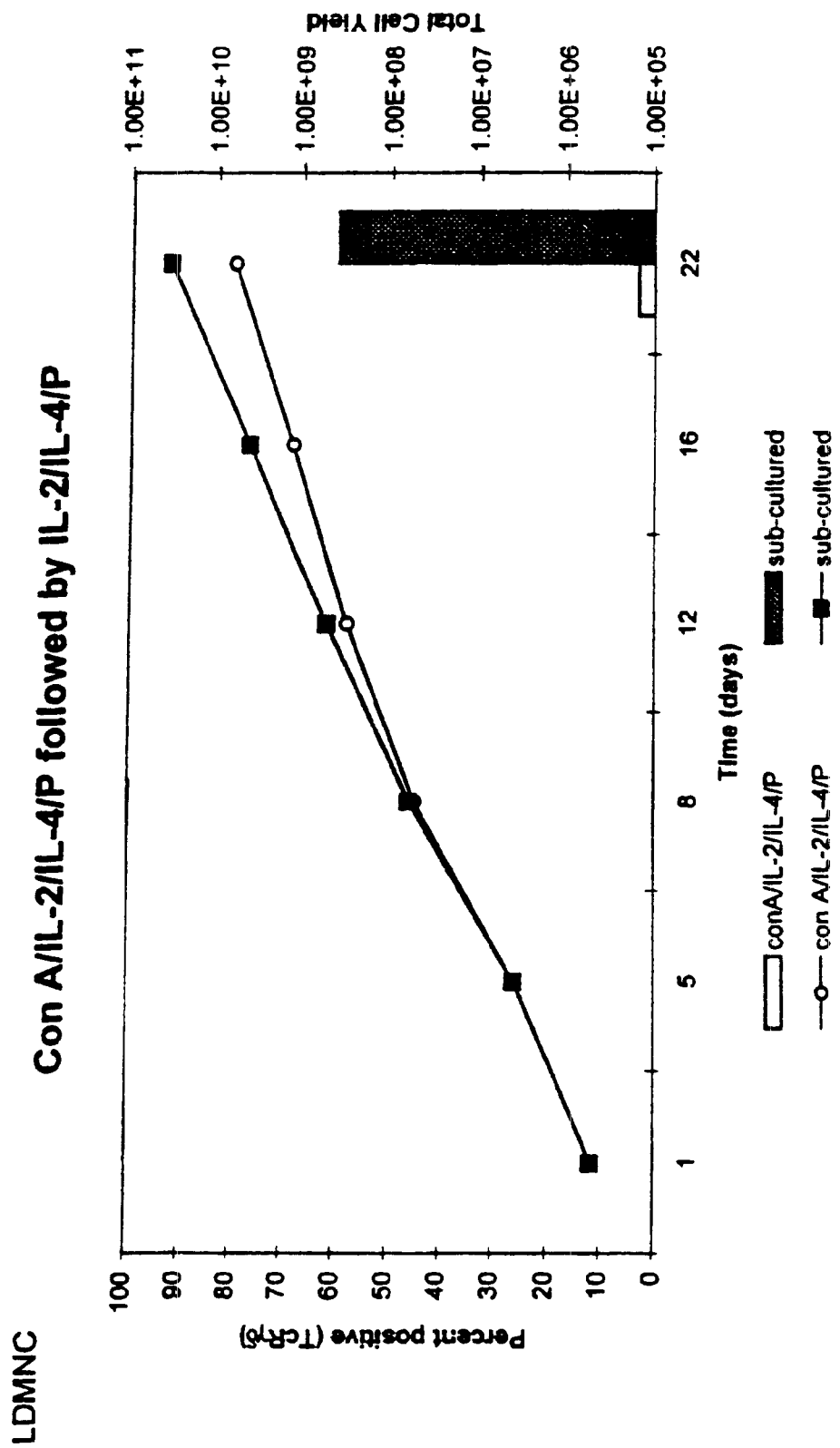

METHODS FOR THE PRODUCTION OF TCRγδ+ T CELLS

This application claims benefit of Provisional Number 60/107,006 filed Nov. 4, 1998.

FIELD OF THE INVENTION

The present invention relates to novel culture methods for the ex vivo expansion of TcRγδ+ T cells.

BACKGROUND OF THE INVENTION

TcRγδ+ cells are a small subset of circulating T lymphocytes that are distinct from conventional TcRαβ+ T cells which recognize, with fine specificity, foreign peptide antigens in the context of classical class I or class II major histocompatibility complex (MHC) restriction elements. By contrast, TcRγδ+ T cells are able to recognize both peptide and non-peptide antigens which may be derived from either foreign microorganisms or endogenous cellular products induced by stress such as viral infection or transformation. Moreover, unlike antigen recognition by TcRαβ+ T cells, antigen recognition by TcRγδ+ T cells is not MHC-restricted.

The T cell receptors of TcRαβ+ and TcRγδ+ T cells are distinguished by the different genetic elements that encode them. The majority of TcRγδ+ T cells are classified into two main subsets, Vδ1+ and Vδ2+, based on the genes that encode their δ chain. The major subset of TcRγδ+ T cells in human peripheral blood expresses Vδ2 in combination with Vγ9, while most of the remainder express Vδ1 in combination with Vγ2, Vγ3, Vγ4, Vγ5 or Vγ8 (Salerno, A. and Dieli, F., 1998).

Since TcRγδ+ T cells lack the fine specificity characteristics of TcRαβ+ T cells, it has been proposed that they represent a more primitive immune mechanism that provides a first-line surveillance function against infection and tumours (Boismenu, R. et al., 1997). Several studies have documented the response of TcRγδ+ T cells to various viruses, bacteria and parasites (Bukowski, J. F. et al., 1994; Wallace, M. et al., 1995; Lang, F. et al., 1995; Elloso, M. M. et al., 1996) as well as their ability to mediate lysis of tumour cells of various origins (Zocchi, M. R. et al., 1990; Kitayama, J. et al., 1993; Choudhary, A. et al., 1995). Hematopoietic tumours may be particularly susceptible to the lytic effects of TcRγδ+ T cells, since transgenic mice expressing the Vγ1.1 transgene display spontaneous resistance to injected T cell leukemias, and TcRγδ+ T cell hybridomas derived from these mice preferentially respond to hematopoietic malignant cells over non-hematopoietic tumour cells (Penninger, J. et al., 1995). Moreover, human TcRγδ+ T cells clones derived from patient peripheral blood and bone marrow have been shown to lyse autologous leukemic cells in acute lymphoblastic leukemia and acute myeloid leukemia, respectively (Bensussan, A. et al., 1989; Jahn, B. et al., 1995). Furthermore, improved disease-free survival in leukemia patients after allogeneic bone marrow transplantation has been shown to be associated with an increase in the number and percentage of TcRγδ+ T cells in peripheral blood (Lamb, L. S. et al., 1996). Collectively, these results suggest that TcRγδ+ T cells may have therapeutic potential in the treatment of cancer and infectious diseases.

Many of the published methods describing the ex vivo expansion of TcRγδ+ T cells require the presence of antigen. Virus-infected or transformed cells or cell lines, bacteria and parasites have been shown to stimulate TcRγδ+ T cell expansion ex vivo, as have established tumour cell lines. For example, herpes simplex virus (HSV)-infected cells were used to stimulate the expansion of Vδ2+ cells (Bukowski, J. F. et al., 1994), while Epstein-Barr virus (EBV)-transformed B-lymphoblastoid cell lines were used to stimulate the expansion of Vδ1+ cells (Orsini, D. L. M. et al., 1993). Extracts of *Mycobacterium tuberculosis* and blood-stage *Plasmodium falciparum* malarial antigens have been shown to stimulate proliferation of TcRγδ+ T cells (Constant, P. et al., 1994; Elloso, M. M. et al., 1996). Daudi, an immortalized human Burkitt's lymphoma cell line, can also stimulate the proliferation of TcRγδ+ T cells (Kaur, I. et al., 1993). In addition, well-characterized, non-peptidyl antigens of the prenyl phosphate family, for example, isopentenyl pyrophosphate, have been shown to stimulate the ex vivo expansion of TcRγδ+ T cells (Garcia, V. E. et al., 1998). In some of these systems, the antigen-stimulated cultures of TcRγδ+ T cells were supplemented with IL-2, IL-4 or other cytokines.

TcRγδ+ T cells have also been expanded ex vivo from populations of tumour infiltrating lymphocytes (TIL) by culture with IL-2 (Zocchi, M. R. et al., 1990) or IL-2 in combination with immobilized anti-CD3 antibody (Kitayama, J. et al., 1993) or anti-TcRγδ antibody (Yu, S. et al., 1999). In these systems, selective stimulation of the TcRγδ30 T cells by the tumour antigens is presumed to have occurred in vivo prior to isolation of T cells from the cancerous tissue.

In another system, TcRγδ+ T cells were expanded from the peripheral blood of glioblastoma patients using a solid-phase, immobilized anti-CD3 antibody in combination with IL-2 followed by culture in IL-2 alone (Yamaguchi, T., et al, 1997). These authors reported that the subsequently purified TcRγδ+ T cells did not proliferate for more than one week in the presence of IL-2 alone and therefore, they concluded, that this method would be applicable only to short term studies. They further showed that the method resulted in the expansion and enrichment of both TcRγδ+ and TcRαβ+ T cells, achieving TcRγδ+ T cell purities on the order of 28%. In a subsequent report, the same authors demonstrated that this method selectively expanded the Vδ2+ subset (Suzuki, Y., et al, 1999).

Thus, there are limitations to cell proliferation and/or requirements for antigen stimulation in the existing methods for ex vivo culture and expansion of TcRγδ+ T cells. Furthermore, while many papers report the expansion of the Vδ2+ cell subset, few papers report the expansion of the Vδ1+ cell subset and none report the simultaneous expansion of both the Vδ2+ and Vδ1+ T cell subsets in a single culture.

In view of the foregoing, there is a need in the art for a method to selectively culture large amounts of TcRγδ+ cells in vitro.

SUMMARY OF THE INVENTION

The present invention provides novel methods for expanding TcRγδ+ T cells in culture in the absence of exogenous antigen. Accordingly, the present invention provides a method for expanding TcRγδ+ T cells in a starting sample comprising:
  (1) culturing cells in the starting sample in a first culture medium comprising a T cell mitogen and at least two cytokines; and
  (2) culturing the cells obtained in step (1) in a second culture medium comprising at least two cytokines to expand TcRγδ+ T cells.

In one embodiment, the present invention provides a method for expanding TcRγδ+ T cells in a starting sample comprising:

(1) culturing cells in the starting sample in a first culture medium comprising (a) a T cell mitogen, (b) interleukin-2 and (c) interleukin-4; and (2) culturing the cells obtained in step (1) in a second culture medium comprising (i) interleukin-2 and (ii) interleukin-4 to expand TcRγδ+ T cells.

In another embodiment, the present invention provides a method for expanding TcRγδ+ T cells in a starting sample comprising:

(1) obtaining low density mononuclear cells (LDMNC) from the starting sample;

(2) culturing the cells obtained in step (1) in a first culture medium comprising (a) a T cell mitogen, (b) interleukin-2 and (c) interleukin-4; and (3) culturing the cells obtained in step (2) in a second culture medium comprising (i) interleukin-2 and (ii) interleukin-4 to expand TcRγδ+ T cells.

In a preferred embodiment, prior to culturing the cells in the first culture medium, the cells are depleted of non-CD4+ cells or non-TcRγδ+ cells.

In a further embodiment, the present invention provides a method for expanding TcRγδ+ T cells in a starting sample comprising:

(1) culturing cells in the starting sample in a first culture medium comprising a leukocyte conditioned medium; and (2) culturing the cells obtained in step (1) in a second culture medium comprising (i) interleukin-2 and (ii) interleukin-4 to expand TcRγδ+ T cells.

In yet another embodiment, the present invention provides a method for expanding TcRγδ+ T cells in a starting sample comprising:

(1) obtaining low density mononuclear cells (LDMNC) from the starting sample;

(2) culturing the cells obtained in step (1) in a first culture medium comprising a leukocyte conditioned medium; and (3) culturing the cells obtained in step (2) in a second culture medium comprising (i) interleukin-2 and (ii) interleukin-4 to expand TcRγδ+ T cells.

The TcRγδ+ T cells obtained by the method of the invention can be used in a variety of experimental, therapeutic and commercial applications.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 5 is a graph showing the total cell yields and the percentages of TcRγδ+ T cells at various times during culture of LDMNC with conA/IL-2/IL-4/P or with conA/IL-2/IL-4/P followed by sub-culture with IL-2/IL-4/P.

DETAILED DESCRIPTION OF THE INVENTION

Figure 1:
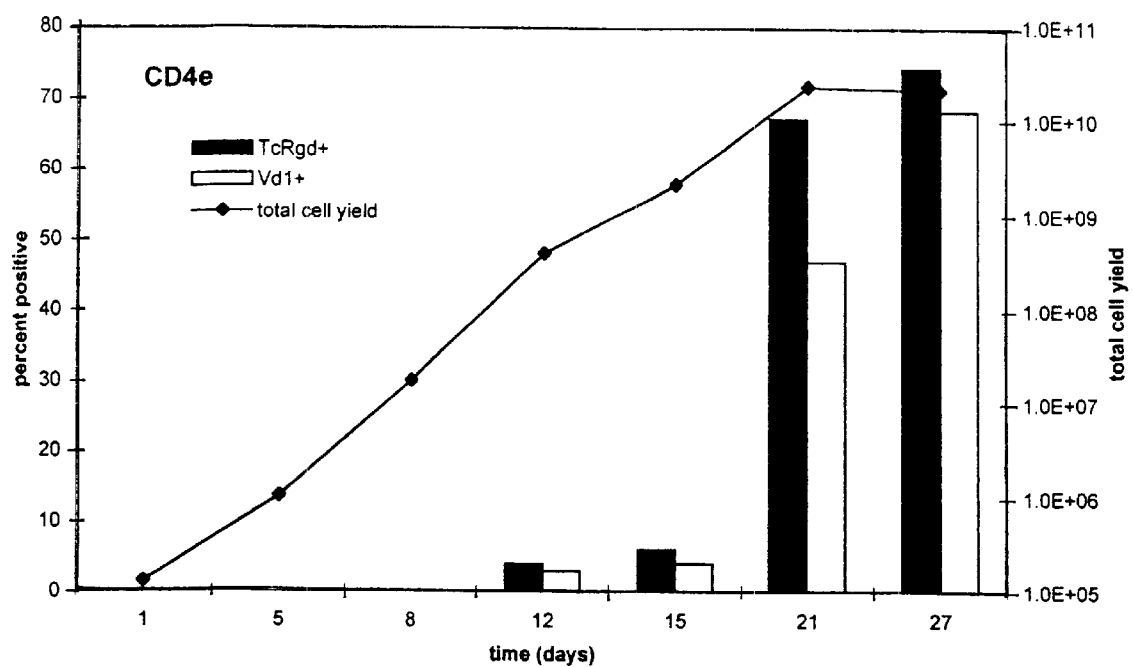
FIG. 1 is a graph showing the total cell yield and the percentage of TcRγδ+ and Vδ1+ T cells at various times during culture of CD4-enriched cells with XLCM/P.

The present invention provides novel methods for selectively expanding TcRγδ+ T cells in culture. The methods can use either unfractionated starting samples or starting samples which have been enriched for T cells. Advantageously, the methods of the invention do not require the use of antigenic stimulation which is necessary in most other procedures.

Accordingly, the present invention provides a method for expanding TcRγδ+ T cells in a starting sample comprising:

(1) culturing cells in the starting sample in a first culture medium comprising a T cell mitogen and at least two cytokines; and (2) culturing the cells obtained in step (1) in a second culture medium comprising at least two cytokines to expand TcRγδ+ T cells.

The two cytokines in the first and second culture media may be the same or different. Preferably, the two cytokines are the same, more preferably the two cytokines are interleukin-2 and interleukin-4.

In one aspect, the present invention provides a method for expanding TcRγδ+ T cells in a starting sample comprising:

(1) culturing cells in the starting sample in a first culture medium comprising (a) a T cell mitogen, (b) interleukin-2 and (c) interleukin-4; and (2) culturing the cells obtained in step (1) in a second culture medium comprising (i) interleukin-2 and (ii) interleukin-4 to expand TcRγδ+ T cells.

The starting sample can be any sample that contains TcRγδ+ T cells or precursors thereof including, but not limited to, blood, bone marrow, lymphoid tissue, epithelia, thymus, liver, spleen, cancerous tissues, lymph node tissue, infected tissue, fetal tissue and fractions or enriched portions thereof. The starting sample is preferably blood including peripheral blood or umbilical cord blood or fractions thereof, including buffy coat cells, mononuclear cells and low density mononuclear cells (LDMNC). The cells may be obtained from a starting sample of blood using techniques known in the art such as density gradient centrifugation. For example, whole blood may be layered onto an equal volume of Ficoll-Hypaque™ followed by centrifugation at 400×g for 30 minutes at room temperature. The interface material will contain the low density mononuclear cells which can be collected and washed in culture medium and centrifuged at 100×g for 10 minutes at room temperature. Prior to culturing for TcR$\gamma\delta^+$ cells, the cells can be maintained in any suitable mammalian culture medium such as AIM-V™, RPMI 1640 or IMDM.

Prior to culturing the starting sample or fraction thereof (such as LDMNC) in the first culture medium, the sample or fraction thereof may be enriched for certain cell types and/or depleted for other cell types.

In particular, the starting sample or fraction thereof may be enriched for CD4$^+$ cells or may be enriched for T cells together with the depletion of TcR$\alpha\beta^+$ T cells. The sample may be enriched or depleted of certain cell types using techniques known in the art. In one embodiment, the cells of a particular phenotype may be depleted by culturing the starting sample or fraction thereof with an antibody cocktail containing antibodies specific for markers on the cells to be depleted. Preferably, the antibodies in the cocktail are tetrameric antibody complexes as described in U.S. Pat. No. 4,868,109 to Lansdorp.

Once the cells in the starting sample have been fractionated and enriched, if desired, the cells are cultured in a first culture medium comprising a T cell mitogen and at least two cytokines, preferably interleukin-2 (IL-2) and interleukin-4 (IL-4). Preferably, the T cell mitogen is present in an amount from about 0.01 to about 100 µg/ml; the IL-2 is present in an amount from about 0.1 to about 1000 ng/ml; the IL-4 is present in an amount from about 0.1 to about 1000 ng/ml. More preferably, the T cell mitogen is present in an amount from about 0.1 to about 50 µg/ml; the IL-2 is present in an amount from about 1 to about 100 ng/ml; the IL-4 is present in an amount from about 1 to about 100 ng/ml. Even more preferably, the T cell mitogen is present in an amount from about 0.5 to about 10 µg/ml; the IL-2 is present in an amount from about 2 to about 50 ng/ml; the IL-4 is present in an amount from about 2 to about 50 ng/ml. Most preferably, the medium comprises 1 µg/mL of a T cell mitogen; 10 ng/mL IL-2 and 10 ng/mL IL-4.

The cells are preferably cultured in the first culture medium for a period of time ranging from about 3 days to about 21 days. More preferably, from about 5 days to about 14 days.

The T cell mitogen can be any agent that can stimulate T cells including, but not limited to, lectins of plant and non-plant origin, monoclonal antibodies that activate T cells, and other non-lectin/non-antibody mitogens. A preferred plant lectin is concanavalin A (ConA) although other plant lectins such as phytohemagglutinin (PHA) may be used. A preferred antibody is an anti-CD3 antibody such as OKT3. Other mitogens include phorbol 12-myristate-13-acetate (TPA) and its related compounds, mezerein, Staphylococcal enterotoxin A (SEA) and Streptococcal protein A. The T cell mitogen is preferably added to the culture in a soluble form, for example, dissolved in culture medium.

Following culture in the first culture medium, the cells are washed by centrifugation and sub-cultured in a second culture medium comprising at least two cytokines, preferably interleukin-2 (IL-2) and interleukin-4 (IL-4). In the second culture medium, both IL-2 and IL-4 are required for maximum cell expansion. If the cells are sub-cultured with IL-2 alone then proliferation continues for a few days but then quickly abates; if the cells are sub-cultured with IL-4 alone then the continued proliferation is even less. Thus, for continued cell proliferation following the removal of the mitogen, both IL-2 and IL-4 in the second culture medium are essential.

The sub-culture step is important for the expansion of TcR$\gamma\delta^+$ T cells by the method of the present invention particularly if the starting sample or LDMNC are not fractionated prior to culture in the first culture medium. If the LDMNC are fractionated then the subculture step may be optional. If LDMNC are continuously cultured in conA/IL-2/IL-4 (with no sub-culture in IL-2/IL-4), then only TcR$\alpha\beta^+$ T cells will expand (see Example 4). The sub-culture in IL-2/IL-4 (i.e. the removal of the T cell mitogen, con A) results in the outgrowth of TcR$\gamma\delta^+$ T cells. Conversely, if con A is left out of the first culture medium, no cell expansion occurs at all. The removal of con A by sub-culture has the further advantage of making the TcR$\gamma\delta^+$ T cells better suited for therapeutic use, as the administration of residual concanavalin A to a patient is not desirable. The removal of the T cell mitogen in the subculturing step may not be required if the TcR$\gamma\delta^+$ T cells are for experimental, diagnostic or other non-therapeutic uses.

Preferably, in the second culture medium, the IL-2 is present in an amount from about 0.1 to about 1000 ng/ml; and the IL-4 is present in an amount from about 0.1 to about 1000 ng/ml. More preferably, the IL-2 is present in an amount from about 1 to about 100 ng/ml; and the IL-4 is present in an amount from about 1 to about 100 ng/ml. Even more preferably, the IL-2 is present in an amount from about 2 to about 50 ng/ml; and the IL-4 is present in an amount from about 2 to about 50 ng/ml. Most preferably, the second culture medium comprises 10 ng/mL IL-2 and 10 ng/mL IL-4.

The LDMNC are preferably cultured in the second culture medium for a period of time ranging from about 3 days to about 21 days. More preferably, from about 9 days to about 13 days.

The first and second culture media may additionally include other ingredients that can assist in the growth and expansion of the TcR$\gamma\delta^+$ T cells. Examples of other ingredients that may be added, include, but are not limited to, plasma or serum, additional growth factors including cytokines such as IL-12, IL-15, tumour necrosis factors (TNFs) and interferons (IFNs), purified proteins such as albumin, a lipid source such as low density lipoprotein (LDL), vitamins, amino acids, steroids and any other supplements supporting or promoting growth and/or survival.

Preferably, both the first and second culture media are supplemented with serum or plasma (P). The amount of P in the first and second culture media is preferably from about 1% to about 25%. More preferably, the amount of P in the first and second culture media is from about 2% to about 20%. Even more preferably, the amount of P in the first and second culture media is from about 2.5% to about 10%. Most preferably, the amount of P in the first and second culture media is 5%. The serum or plasma (P) can be obtained from any source including, but not limited to, human peripheral blood, umbilical cord blood, or blood derived from another mammalian species. The plasma may be from a single donor or may be pooled from several donors. If autologous TcR$\gamma\delta^+$ T cells are to be used clinically, i.e. re-infused into the same patient from whom the original starting sample was obtained, then it is preferable to use autologous P as well (i.e. from the same patient) to avoid the introduction of extraneous products (e.g. viruses) into that patient. If the TcRγδ+ T cells are to be used allogeneically (i.e. infused into a person other than the one from whom the original starting sample was obtained) then it is preferable to use plasma from one or the other to minimize the introduction of extraneous products into the patient; at a minimum the plasma should be human-derived to avoid the administration of animal products to the patient.

In another aspect of the invention, the T cell mitogen and at least two cytokines in first culture medium may be derived from a leukocyte conditioned medium such as XLCM. XLCM™ is a conditioned medium prepared from umbilical cord blood as described in Example 1 and contains a T cell mitogen (ConA) and several cytokines. XLCM contains only low amounts of IL-2 and almost undetectable IL-4.

Accordingly, the present invention provides a method for expanding TcRγδ+ T cells in a starting sample comprising:
(1) culturing cells in the starting sample in a first culture medium comprising a leukocyte conditioned medium; and
(2) culturing the cells obtained in step (1) in a second culture medium comprising (i) interleukin-2 and (ii) interleukin-4 to expand TcRγδ+ T cells.

Preferably, prior to culturing the cells in the starting sample in step (1), the cells are enriched for T cells as described above.

In a preferred embodiment the leukocyte conditioned medium is XLCM. The XLCM is preferably present in the first culture medium in an amount from about 1% to about 25%. More preferably, XLCM is present in the first culture medium in an amount from about 2% to about 20%. Even more preferably, XLCM is present in the first culture medium in an amount from about 2.5% to about 10%. Most preferably, the first culture medium contains 5% XLCM. The amounts of IL-2 and IL-4 in the second culture medium are preferably as described above. The first and second culture media preferably contain serum or plasma as described above.

The methods of the invention result in expanded cell populations of TcRγδ+ T cells. By "expanded" it is meant that the number of the desired or target cell type (i.e., TcRγδ+ T cells) in the final preparation is higher than the number in the initial or starting cell population.

The TcRγδ+ T cells obtained according to the methods of the invention can be separated from other cells that may be present in the final culture using techniques known in the art including fluorescence activated cell sorting, immunomagnetic separation, affinity column chromatography, density gradient centrifugation and cellular panning.

The present invention includes the TcRγδ+ T cells obtained by the methods of the invention. Accordingly, the present invention provides a cell preparation of TcRγδ+ T cells. Preferably, the TcRγδ+ T cells comprise greater than 60%, more preferably greater than 80% and most preferably greater than 90%, of the total cells in the enriched population.

In contrast to the methods of the prior art, both Vδ1+ and Vδ2+ TcRγδ+ T cells are expanded by the methods of the invention. Accordingly, the present invention provides a cell preparation of TcRγδ+ T cells which comprises Vδ1+ and Vδ2+ TcRγδ+ T cells. Preferably, the cell preparation comprises about 50–90% Vδ1+ TcRγδ+ T cells and about 10–50% Vδ2+ TcRγδ+ T cells of the total TcRγδ+ T cells in the preparation. More preferably the cell preparation comprises about 70% Vδ1+ TcRγδ+ T cells and 30% Vδ2+ TcRγδ+ T cells of the total TcRγδ+ T cells in the preparation. Advantageously, the TcRγδ+ T cell preparations of the present invention are free or substantially free of a T cell mitogen.

The present invention also includes the use of the TcRγδ+ T cells obtained by the method of the invention in any and all applications. TcRγδ+ T cells are thought to be a first line of defense against infectious pathogens. In addition, TcRγδ+ T cells possess intrinsic cytolytic activity against transformed cells of various origins including B-cell lymphomas, sarcomas and carcinomas. As a result, the TcRγδ+ T cells obtained and cultured ex vivo according to the method of the invention, can be transfused into a patient for the treatment or prevention of infections, cancer or diseases resulting from immunosuppression. Advantageously, the TcRγδ+ T cells of the invention do not contain ConA or fetal bovine serum making them useful for human therapeutic applications. Accordingly, the present invention provides a method of modulating an immune response comprising administering an effective amount of TcRγδ+ T cells prepared according to a method of the invention to an animal in need thereof.

The term "effective amount" as used herein means an amount effective, at dosages and for periods of time necessary to achieve the desired results.

The term "animal" as used herein includes all members of the animal kingdom. Preferably, the animal is a mammal, more preferably a human.

In one embodiment, the present invention provides a method of treating an infection comprising administering an effective amount of TcRγδ+ T cells prepared according to the method of the invention to an animal in need thereof.

Examples of infections that may be treated include, but are not limited to, bacterial infections such as those caused by Mycobacteria (e.g. tuberculosis), viral infections such as those caused by herpes simplex virus (HSV), human immunodeficiency virus (HIV) or the hepatitis viruses, and parasitic infections such as those caused by Plasmodium (e.g. malaria).

In another embodiment, the present invention provides a method for treating cancer comprising administering an effective amount of TcRγδ+ T cells prepared according to the method of the invention to an animal in need thereof.

Examples of cancer that may be treated according to the present invention include, but are not limited to, leukemias including chronic myelogenous leukemia, acute myelogenous leukemia, acute lymphoblastic leukemia, and T cell and B cell leukemias, lymphomas (Hodgkins and non-Hodgkins), lymphoproliferative disorders, plasmacytomas, histiocytomas, melanomas, adenomas, sarcomas, carcinomas of solid tissues, hypoxic tumours, squamous cell carcinomas, genitourinary cancers such as cervical and bladder cancer, hematopoietic cancers, head and neck cancers, and nervous system cancers.

In a preferred embodiment, the present invention provides a method of treating chronic myelogenous leukemia comprising administering an effective amount of TcRγδ+ T cells prepared according to the method of the invention to an animal in need thereof. In such an embodiment, the LDMNC can be obtained from a patient with chronic myelogenous leukemia (CML). After culturing and expanding for TcRγδ+ T cells, the isolated cells will not contain any cancerous CML cells making them well suited for re-infusion back to the patient.

The invention also includes the use of the TcRγδ+ T cells obtained by the methods of the invention to modulate an immune response, to treat an infection or to treat cancer as described hereinabove. The invention further includes the use of the TcRγδ+ T cells obtained according to the methods of the invention to prepare a medicament or pharmaceutical composition to modulate an immune response, to treat an infection or to treat cancer as described hereinabove.

The TcRγδ+ T cells isolated according to the present invention can also be used in experimental models, for example, to further study and elucidate the function of the cells. Additionally, these cells may be used for studies directed towards the identification of the antigens/epitopes recognized by TcRγδ+ T cells and for the design and development of vaccines.

The isolated TcRγδ+ T cells, according to the invention may be immediately used in the above therapeutic, experimental or commercial applications or the cells may be cryopreserved for use at a later date.

The following non-limiting examples are illustrative of the present invention:

EXAMPLES

The following methods relate to the large scale, ex vivo expansion of TcRγδ+ T cells in liquid culture in the absence of antigen or accessory cells. The starting material consists of low density mononuclear cells (LDMNC) from human peripheral blood. The LDMNC may be further fractionated by (1) enrichment for CD4+ T cells, (2) enrichment for T cells together with depletion of TcRαβ+ T cells, or (3) not further fractionated. The cells are preferably cultured in medium containing some combination of XLCM, human sera or plasma (P), concanavalin A (con A), interleukin-2 (IL-2), and interleukin-4 (IL-4). At frequent intervals the cells are counted and reseeded with fresh medium, and some combination of XLCM, P, con A, IL-2, and IL-4. The percent of cells expressing a particular surface marker is determined using specific antibodies and flow cytometry.

Example 1

CD4e: XLCM/P=>TcRγδ+ T cells

Low density mononuclear cells (LDMNC) were isolated from adult peripheral blood by density gradient centrifugation using Ficoll-Hypaque (density=1.077 g/ml). A volume of 15 ml of whole blood was layered onto an equal volume of Ficoll-Hypaque in a 50 ml conical tissue culture tube, which was then centrifuged at 400×g for 30 minutes at room temperature. The interphase material containing the mononuclear cells was collected and the cells were washed twice in culture medium (AIM-V containing 20 units/ml of heparin and 50 μM 2-mercaptoethanol; serum-free medium= HCBM-2) by centrifugation at 100×g for 10 minutes at room temperature. The cells were diluted in HCBM-2 containing 10% fetal bovine serum (FBS) and incubated in polystyrene tissue culture flasks overnight at 37° C. and 5% $CO_2$. The next morning, the cells were washed twice by centrifugation and resuspended in HCBM-2. A sample of the cell suspension was diluted 1:20 with 2% acetic acid and the total number of nucleated cells determined using a hemocytometer.

CD4+ T cells (CD4e) were enriched from the LDMNC by negative selection using lineage specific antibodies and immunomagnetic affinity chromatography (StemSep, Stem Cell Technologies, Vancouver, BC). A total of $1.7 \times 10^7$ LDMNC were pelleted by centrifugation and washed twice in phosphate buffered saline (PBS) containing 2% FBS (PBS/FBS). The cells were resuspended in 1 ml of PBS/FBS and a cocktail of lineage specific, monoclonal antibodies was added. The cocktail contained antibodies specific for CD8 (cytotoxic T cells), CD14 (monocytes), CD16 (NK cells), CD19 (B cells), CD56 (NK cells) and glycophorin A (erythroid cells). These were bispecific antibodies with specificity for the lineage specific markers listed and specificity for dextran. The LDMNC were incubated with the bispecific antibodies on ice for 30 minutes following which iron dextran colloid was added and the incubation was continued for a further 30 minutes. The suspension was then subjected to immunomagnetic chromatography, a procedure which removed those cells which had been bound by the antibodies and iron dextran particles. Thus, the cells recovered were an enriched population of CD4+ T cells (CD3+, TcRαβ+) as well as other cells lacking the targeted antigens, including TcRγδ+ T cells. The yield of CD4e obtained was $2 \times 10^6$ cells.

The CD4e cells were expanded in HCBM-2 containing 5% (by volume) XLCM and 5% human umbilical cord blood plasma (P). XLCM is a conditioned medium prepared by stimulating human umbilical cord blood cells with mezerein and concanavalin A (J. Immunotherapy 8:129, 1999; J. Immunotherapy and Stem Cell Research 8:525, 1999; and WO 98 33891). XLCM is a complex mixture of stimulatory and inhibitory factors, at least 23 of which have been measured U. Hematotherapy and Stem Cell Research 8:525, 1999).

The CD4e cells were diluted to $1 \times 10^5$ cells/ml in HCBM-2 containing 5% XLCM and 5% P, and were incubated at 37° C. and 5% $CO_2$ for several days during which time the cells underwent an 8-fold expansion. The cell count and viability were determined by mixing a sample of the resuspended cells with an equal volume of 0.4% trypan blue and counting the unstained (viable) and blue (non-viable) cells using a hemocytometer. To passage the cells, a small volume of the culture was diluted back to $1 \times 10^5$ cells/ml with fresh medium and fresh XLCM and P were added to a final concentration of 5% each; the remainder of the culture was used for flow cytometry analysis or was discarded. Thereafter, the cells were similarly passaged every few days in fresh medium supplemented with 5% XLCM and 5% P. The overall fold of expansion was calculated as the product of the folds of expansion measured at each passage, and the theoretical yield of total viable cells was calculated based on the initial seeding density and volume and the folds of expansion at each passage, assuming all of the cells had been kept in continuous culture. Over a period of about three to four weeks, the cells expanded more than 100,000-fold (FIG. 1).

At each passage, a portion of the expanded cells were analyzed by flow cytometry to determine the percent that expressed TcRγδ and the percent that expressed Vδ1. After 21 days in culture, more than 65% of the cultured cells were TcRγδ+ and the majority (>70%) of these TcRγδ+ T cells were Vδ1+ (FIG. 1). The fraction of TcRγδ+ T cells increased further by day 27 at which point more than 70% of the cultured cells were TcRγδ+ and about 90% of these were Vδ1+.

These TcRγδ+ T cells are believed to be derived from a small population present in CD4e that are preferentially expanded under these conditions.

This was an unexpected and novel finding because:
(a) unfractionated LDMNC expanded continuously in XLCM or XLCM+P are almost entirely TcRαβ+, with few, if any, TcRγδ+ T cells (J. Hematotherapy and Stem Cell Research 8:525, 1999);
(b) with XLCM alone (no plasma), there is no expansion of the TcRγδ+ T cell subset (J. Hematotherapy and Stem Cell Research, 1999); and
(c) without XLCM, no cell expansion occurs.

Example 2

TcABd: XLCM/P=>TcRγδ+ T cells

LDMNC were isolated from adult peripheral blood as described in Example 1. TcRγδ+ T cells were enriched from the LDMNC by negative selection using a procedure similar to that described in Example 1, except that the antibody cocktail consisted of a T cell enrichment cocktail (Te) combined with a TcRαβ+ T cell depletion antibody (ABd). The T cell enrichment cocktail consisted of antibodies specific for CD14 (monocytes), CD16 (NK cells), CD19 (B cells), CD56 (NK cells) and glycophorin A (erythroid cells). From a starting number of $1.7 \times 10^7$ LDMNC, a total of $1.3 \times 10^5$ TeABd cells were obtained.

The TeABd cells were cultured in HCBM-2 with 5% XLCM and 5% P as described in Example 1.

Figure 2:
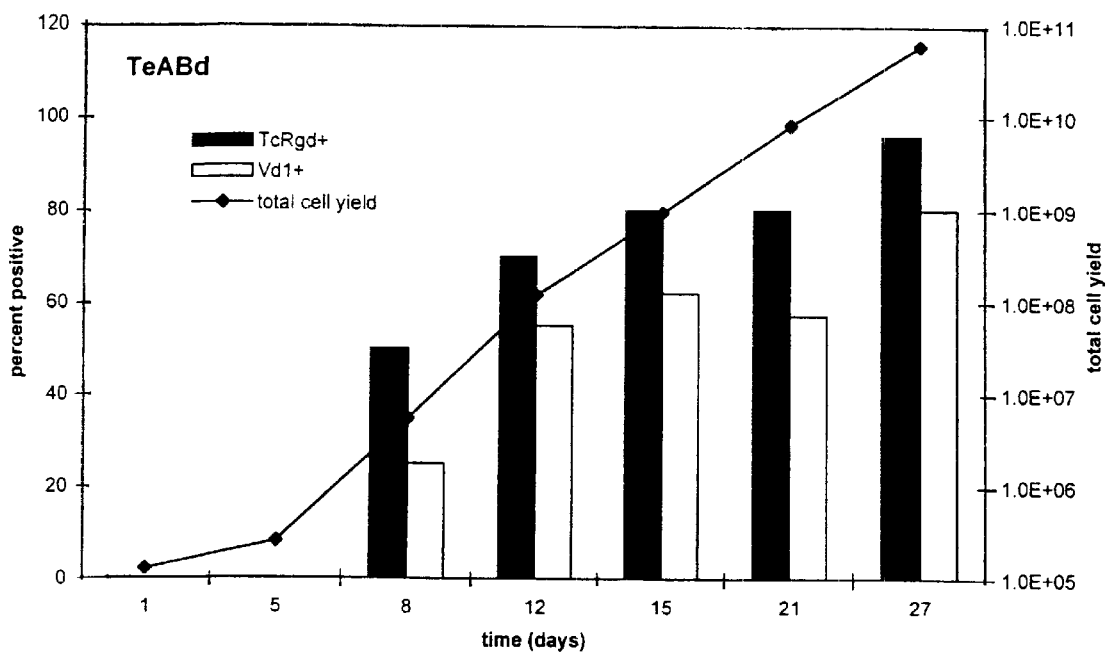
FIG. 2 is a graph showing the total cell yield and the percentage of TcRγδ+ and Vδ1+ T cells at various times during culture of T cell-enriched/TcRαβ-depleted cells with XLCM/P.

Over a period of approximately 4 weeks, the cells underwent an expansion in excess of 100,000-fold (FIG. 2). From day 8 of culture, the expanded cells were >50% TcRγδ+, and reached purities of >80% after day 12. Again, the majority of the TcRγδ+ T cells were Vδ1+ (>70%).

The method of Example 2 follows logically from the method of Example 1: if TcRγδ+ T cells can be expanded from a small sub-population of cells present in CD4e, then they should also be expanded from a relatively more enriched population present in TeABd.

Advantages of the Method Described in Example 2

By the method of Example 2, the TcRγδ+ T cells expanded more rapidly, expanded to greater levels, and were more pure, compared to those obtained using the method of Example 1.

Example 3

LDMNC: XLCM/P->IL-2/IL-4/P or IL-2/P or IL-4/P or P

LDMNC were isolated from adult peripheral blood as described in Example 1 and were cultured without further fractionation or enrichment.

The LDMNC were expanded for 4 days in HCBM-2 containing 5% XLCM, following which they were pelleted and washed by centrifugation, and divided into five equal portions. One portion was sub-cultured in HCBM-2 containing 5% XLCM and 5% P; one portion was sub-cultured in HCBM-2 containing 10 ng/ml IL-2+10 ng/ml IL-4+5% P; one portion was sub-cultured in HCBM-2 containing 10 ng/ml IL-2+5% P; one portion was sub-cultured in HCBM-2 containing 10 ng/ml IL-4+5% P; one portion was sub-cultured in HCBM-2 containing 5% P alone.

Figure 3:
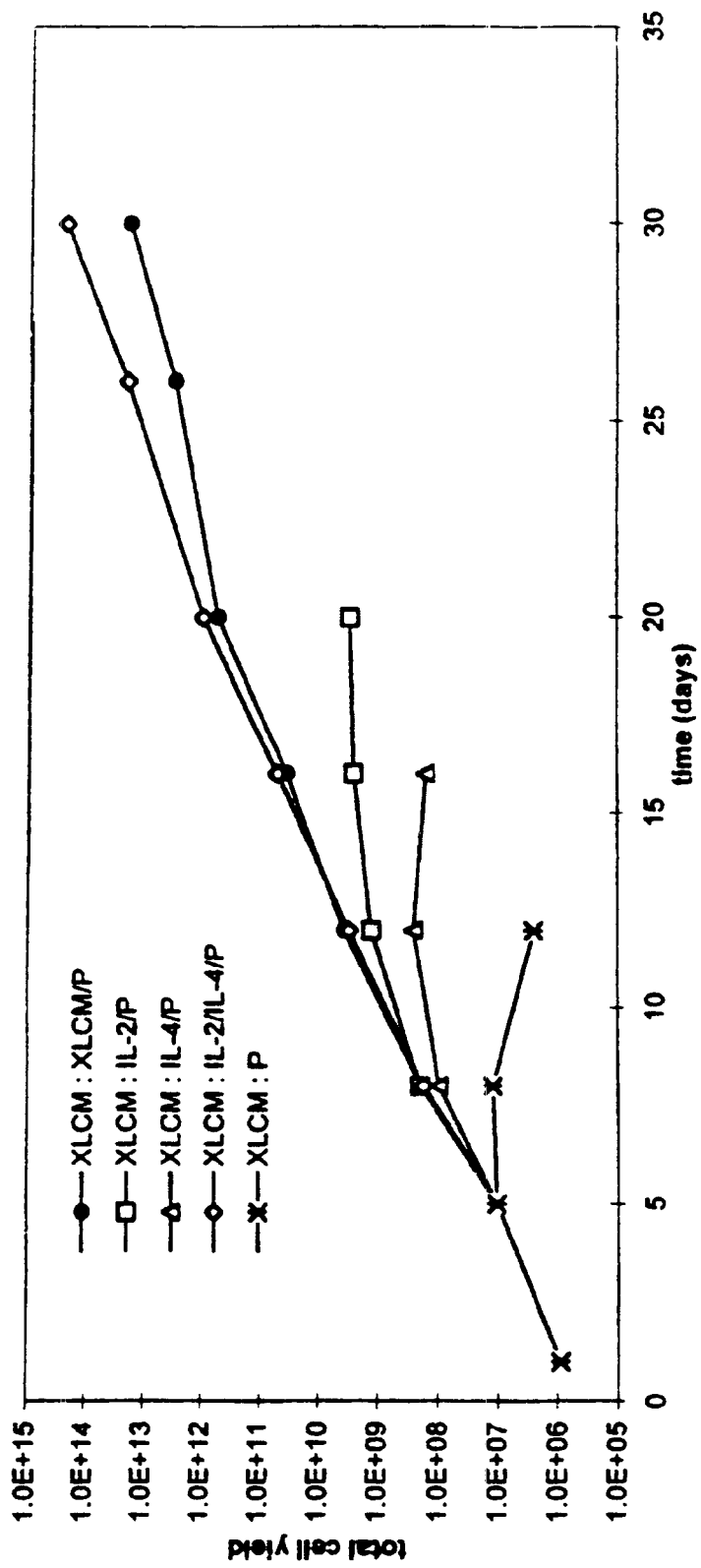
FIG. 3 is a graph showing the total cell yields at various times during culture of LDMNC with XLCM followed by sub-culture with XLCM/P, IL-2/IL-4/P, IL-2/P, IL-4/P or P alone.

The cells sub-cultured with IL-2+IL-4+P expanded as well or better than those continuously cultured in the presence of XLCM, while those sub-cultured with P alone quickly expired (FIG. 3). The cells sub-cultured with IL-2+P expanded for a short while at a low rate and then stopped growing entirely. The cells sub-cultured with IL-4+P expanded even less than those sub-cultured with IL-2+P.

These results demonstrate that both IL-2 and IL-4 are necessary to achieve maximum cell expansion.

Example 4

LDMNC: XLCM/P->IL-2/IL-4/P=>TcRγδ+ T cells

LDMNC were isolated from adult peripheral blood as described in Example 1 and were cultured without further fractionation or enrichment.

Figure 4:
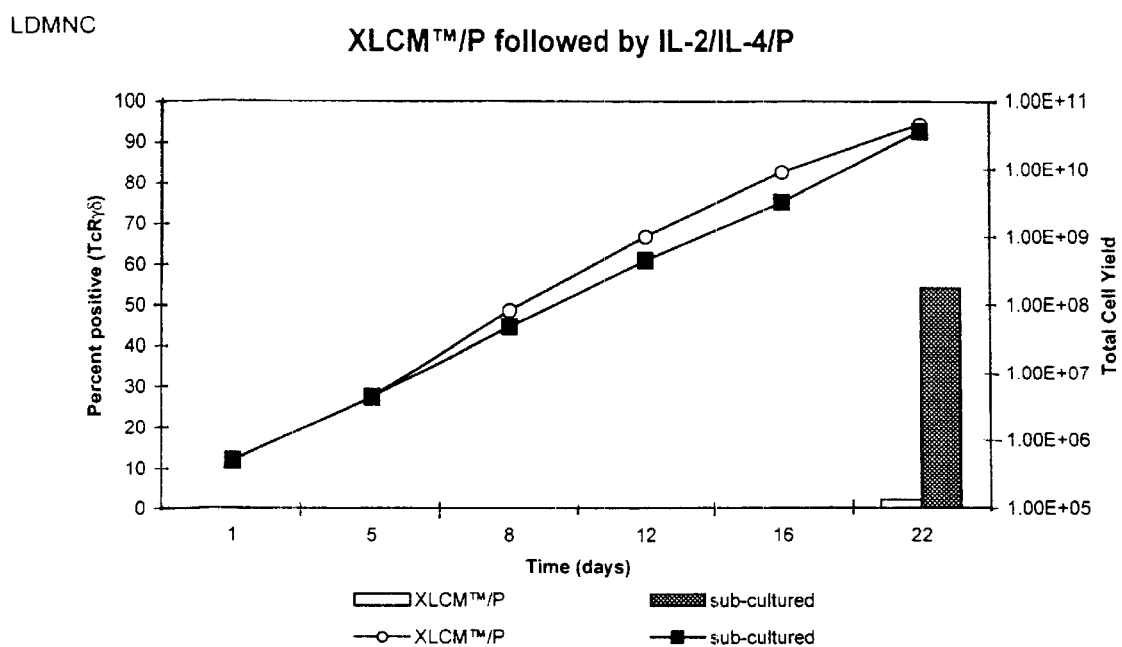
FIG. 4 is a graph showing the total cell yields and the percentages of TcRγδ+ T cells at various times during culture of LDMNC with XLCM/P or with XLCM/P followed by sub-culture with IL-2/IL-4/P.

The LDMNC were expanded for 5 days in HCBM-2 containing 5% XLCM+5% P, following which they were divided, and half were continuously cultured in HCBM-2 containing 5% XLCM+5% P, while the other half were washed and sub-cultured in HCBM-2 containing 10 ng/ml IL-2+10 ng/ml IL-4+5% P. In both cases, the cells expanded more than 100,000-fold in four weeks (FIG. 4). However, flow cytometry analysis revealed that the different conditions gave rise to different kinds of cells: less than 5% of the cells cultured continuously in XLCM/P were TcRγδ+, while more than 50% of the cells cultured in XLCM/P then sub-cultured in IL-2/IL-4/P were TcRγδ+. Note that in this experiment, flow cytometry analysis was performed only on day 22.

The finding of TcRγδ+ T cell expansion under these conditions was completely unexpected. The sub-culture in defined cytokines was done for the purpose of eliminating XLCM, and more specifically residual mezerein and concanavalin A, from the cultured cells. It was found that this technique maintained levels of expansion comparable to those attained by continuous culture in XLCM, but that a different subset, namely the TcRγδ+ T cell subset, was preferentially expanded.

Advantages:

Compared to the methods described in Examples 1 and 2, the method described in Example 4 does not require an initial fractionation or enrichment of the starting cell population, consequently the starting number of cells can be extremely low (e.g. $1 \times 10^5$). In addition, the sub-culture technique eliminates XLCM and its components, e.g. concanavalin A, mezerein, and other known or unknown factors, from the cultured cells.

Example 5

LDMNC: ConA/IL-2/IL-4/P->IL-2/IL-4/P=>TcRγδ+ T cells

LDMNC were isolated from adult peripheral blood as described in Example 1 and were cultured without further fractionation or enrichment.

The LDMNC were expanded for 5 days in HCBM-2 containing 1 µg/ml concanavalin A+10 ng/ml IL-2+10 ng/ml IL-4+5% P, following which they were divided, and half were continuously cultured in HCBM-2 containing 1 ug/ml concanavalin A+10 ng/ml IL-2+10 ng/ml IL-4+5% P, while the other half were washed and sub-cultured in HCBM-2 containing 10 ng/ml IL-2+10 ng/ml IL-4+5% P. In both cases, the cells expanded more than 100,000-fold in four weeks (FIG. 5). However, flow cytometry analysis revealed that the different conditions gave rise to different kinds of cells: less than 5% of the cells cultured continuously in concanavalin A+IL-2+IL-4+P were TcRγδ+, while more than 50% of the cells cultured in concanavalin A+IL-2+IL-4+P then sub-cultured in IL-2+IL-4+P were TcRγδ+. Note that in this experiment, flow cytometry analysis was performed only on day 22.

The finding of TcRγδ+ T cell expansion under these conditions was unexpected for the same reasons described in Example 4, that is, the sub-culture in defined cytokines was done for the purpose of eliminating XLCM, and more specifically residual mezerein and concanavalin A, from the cultured cells. It was found that this technique maintained levels of expansion comparable to those attained by continuous culture in XLCM or in concanavalin A+IL-2+IL-4+P, but that a different subset, namely the TcRγδ+ T cell subset, was preferentially expanded.

Advantages:

As in the method described in Example 4, the starting cell number can be very low since no initial fractionation or enrichment of LDMNC is required and the cells are very efficiently expanded. In addition, the culture conditions are completely defined, XLCM is not used at any step in the method, and the cultured cells are never exposed to mezerein.

Example 6

TeABd: Con A/IL-2/IL-4P->IL-2/IL-4/P=>TcRγδ+ T cells

LDMNC were isolated from adult peripheral blood as described in Example 1, and were enriched for TeABd as described in Example 2. The TeABd were expanded as described in Example 5, that is, they were cultured in HCBM-2 containing 1 μg/ml concanavalin A+10 ng/ml IL-2+10 ng/ml IL-4+5% P and then sub-cultured in HCBM-2 containing 10 ng/ml IL-2+10 ng/ml IL-4+5% P. However, instead of passaging the cells by diluting a small volume of the culture in fresh medium plus cytokines and plasma while discarding the rest, the entire volume of the culture was expanded and all cells were kept in a continuous culture of increasing volume.

Figure 6A:
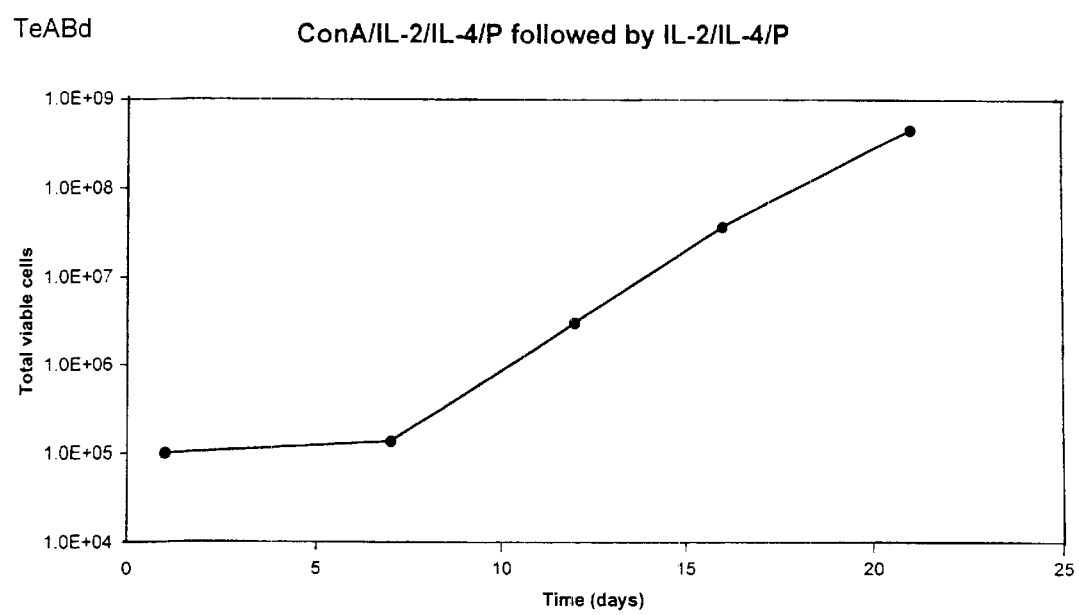
FIG. 6a is a graph showing the total viable cells over time during culture of T cell-enriched/TcRαβ-depleted cells with conA/IL-2/IL-4/P followed by sub-culture with IL-2/IL-4/P.
Figure 6B:
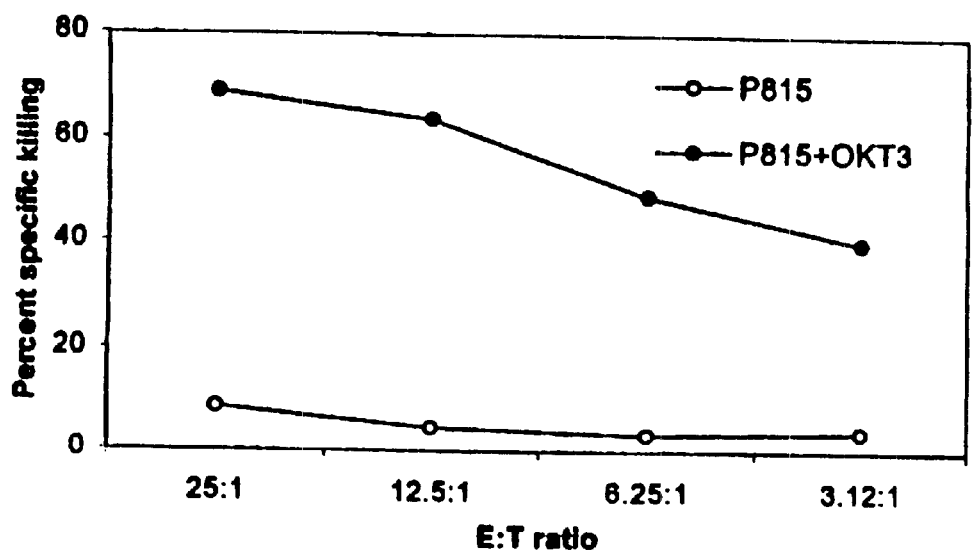
FIGS. 6b–f are graphs showing the percentage killing of various targets by TcRγδ+ effectors at various effector:target ratios.
Figure 6C:
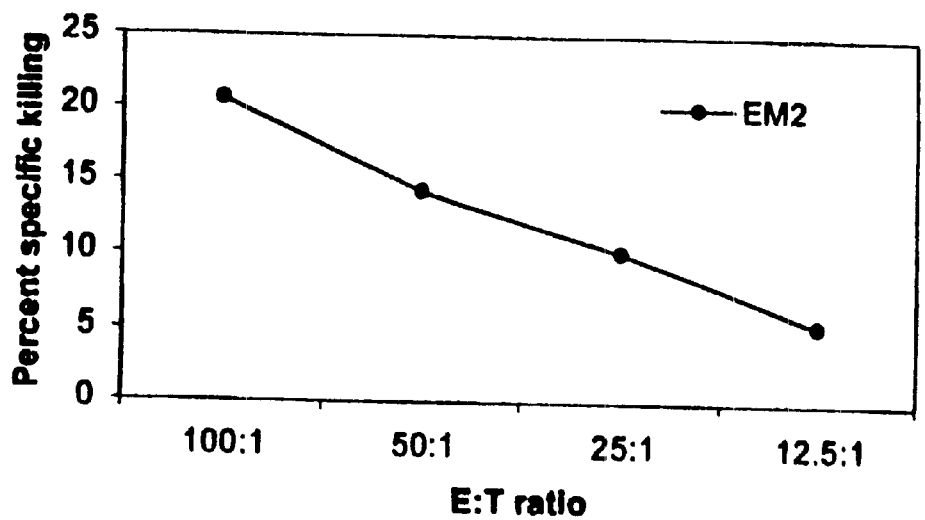
Figure 6D:
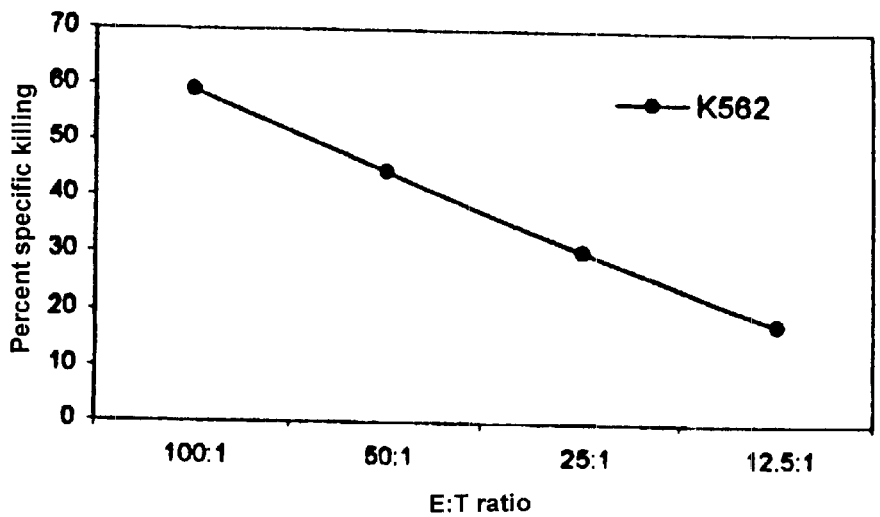
Figure 6E:
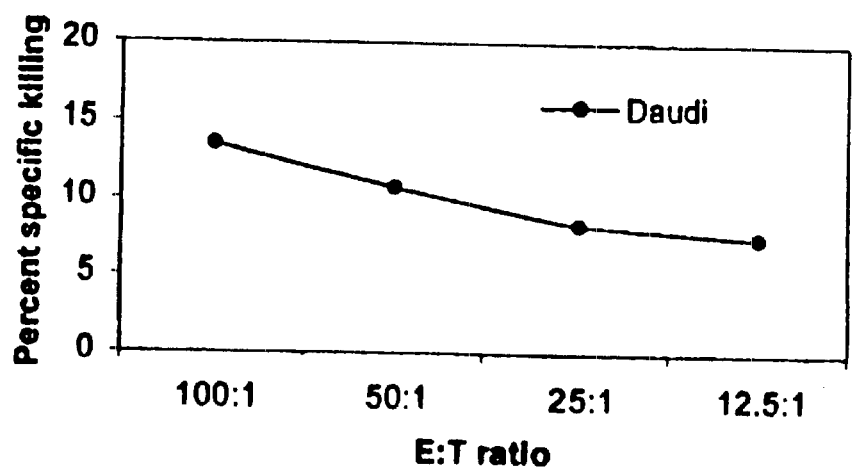
Figure 6F:
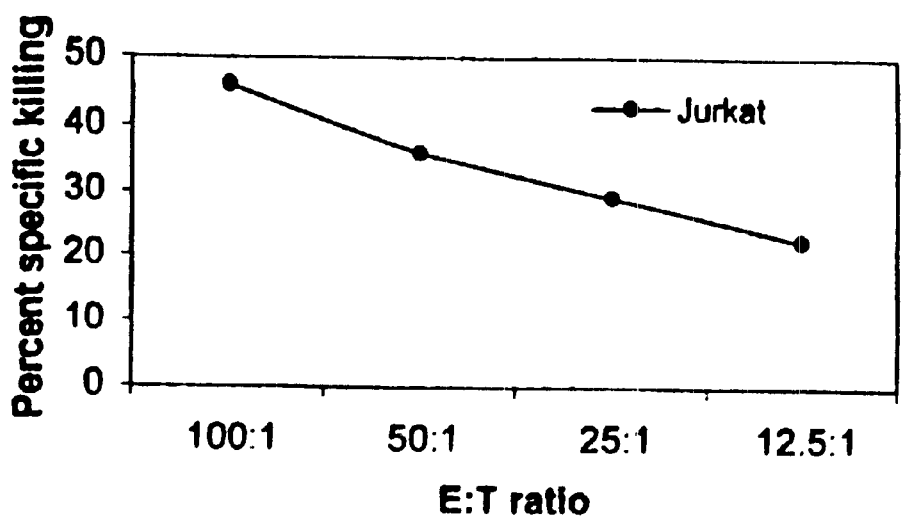
Figure 6G:
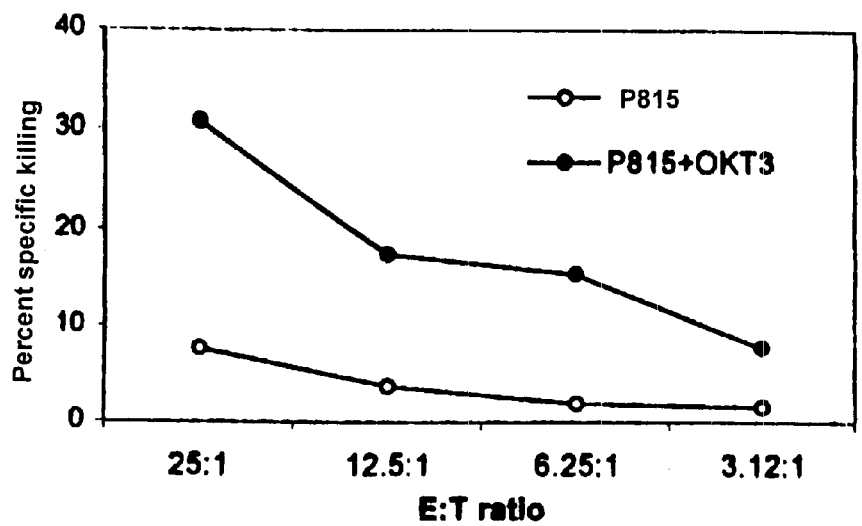
FIGS. 6g–k are graphs showing the percentage killing of various targets by TcRγδ+ effectors at various effector:target ratios after cryopreservation of the effectors.
Figure 6H:
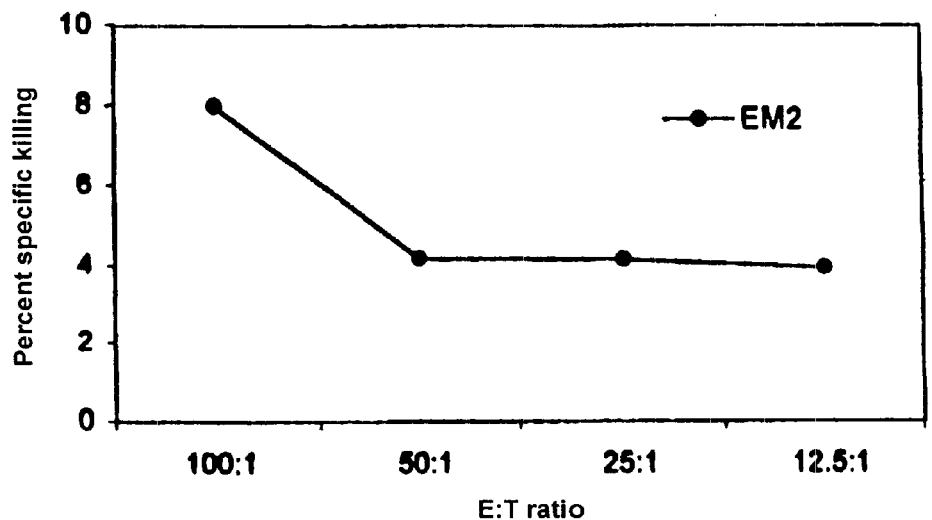
Figure 6I:
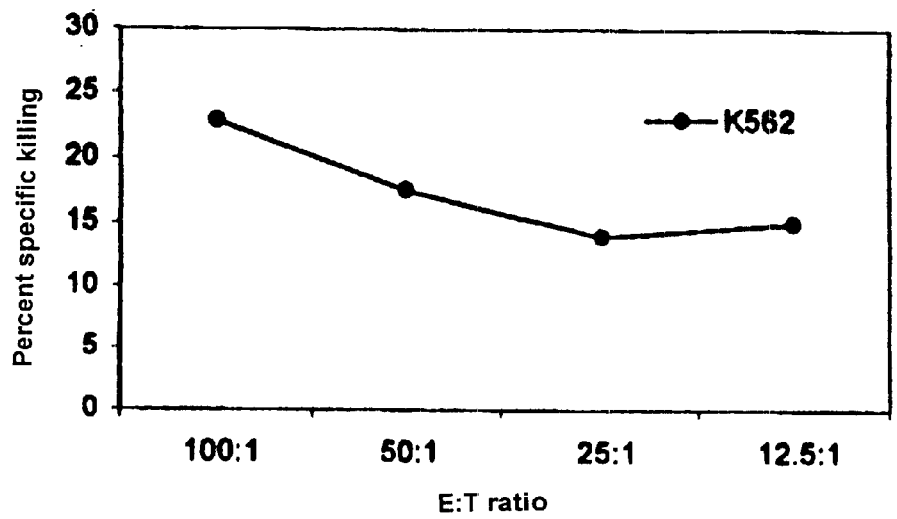
Figure 6J:
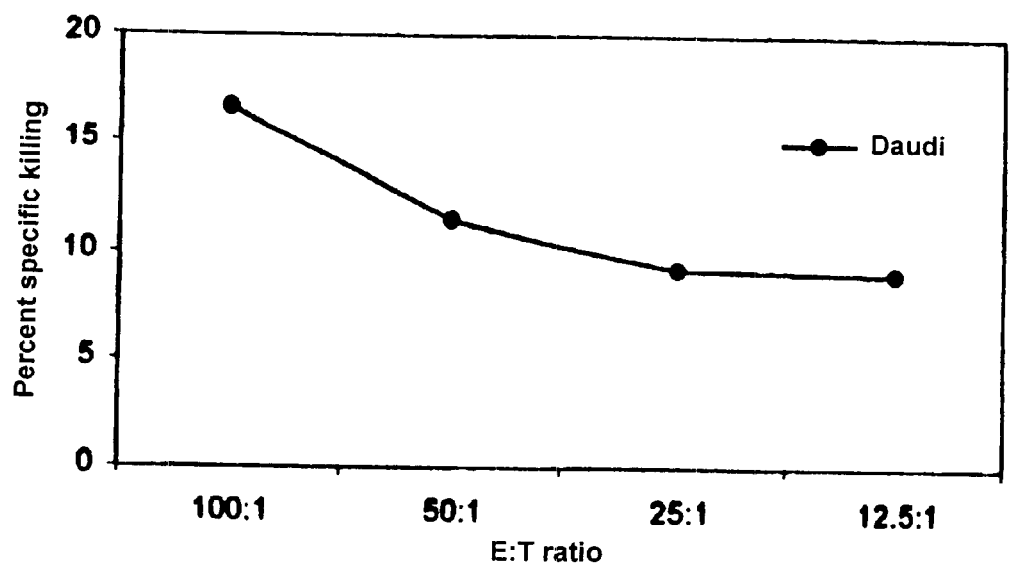
Figure 6K:
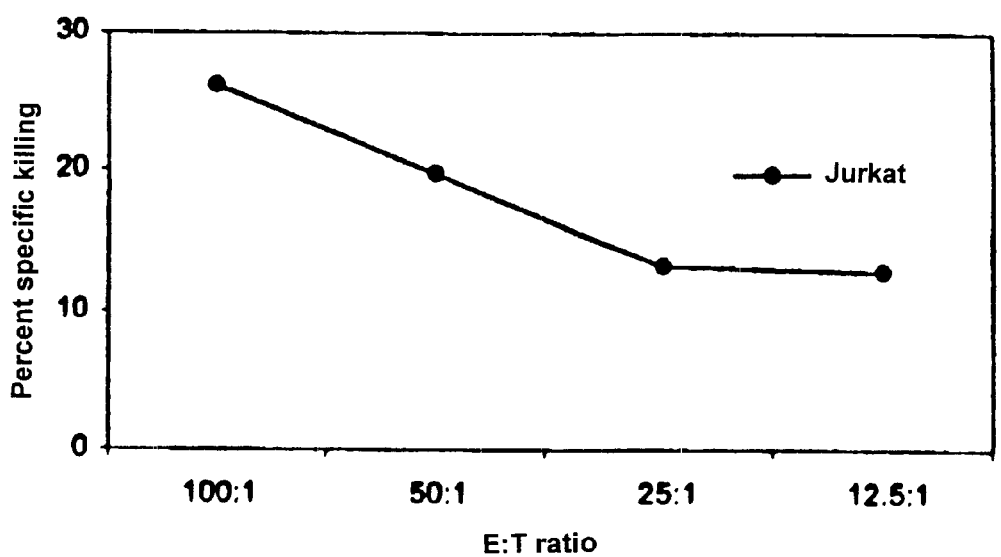

The starting volume of whole blood was 50 ml. The starting number of LDMNC was $3.6 \times 10^7$. The yield of TeABd was $1 \times 10^5$. The TeABd were cultured in concanavalin A+IL-2+IL-4+P for a total of 12 days, by which point they had expanded to a total of $3 \times 10^6$ cells in a total volume of 1.4 ml. At this point, the cultured cells were pelleted by centrifugation and were washed once with HCBM-2. The washed cells were seeded back into culture at $1 \times 10^5$ cells/ml in a total volume of 30 ml and 10 ng/ml IL-2+10 ng/ml IL-4+5% P were added. In this culture, autologous plasma as opposed to allogeneic umbilical cord blood plasma, was used. The cells were further expanded in HCBM-2 containing 10 ng/ml IL-2+10 ng/ml IL-4+5% P for another 9 days. The total culture duration was 21 days. At this point, the cells had expanded to a total of $4.5 \times 10^8$ cells in a total volume of 300 ml (FIG. 6a).

Flow cytometry analysis demonstrated that more than 85% of the cells at day 21 of culture were TcRγδ+ and that the majority of these (>70%) were Vδ1+, while a small, but significant proportion (~10%) were Vδ2+. Furthermore, while about 10% of the cells expressed CD56, less than 3% expressed CD16, indicating that this method did not result in the significant expansion of natural killer (NK) cells.

The cytotoxic activity of the expanded TcRγδ+ T cells was demonstrated using a calcein-release assay. Target cells were labelled with the fluorogenic substrate calcein-AM and were incubated with the TcRγδ+ effector cells at various effector-:target (E:T) ratios. Cytolysis of the target cells was assessed by measuring the release of calcein into the supernatant. Percent specific killing of the targets by the effectors was calculated from the relative fluorescence units (rfu) according to the following formula (where "experimental rfu" is the amount of fluorescence measured due to calcein released from target cells co-incubated with effector cells, "maximum rfu" is the fluorescence obtained from an equal number of target cells lysed with detergent (Triton X-100), and "spontaneous rfu" is the fluorescence obtained from an equal number of target cells incubated in the absence of effector cells or detergent):

Percent specific lysis=experimental rfu−spontaneous rfu× 100 maximum rfu−spontaneous rfu P815 is a mouse mastocytoma cell line that bears receptors for the Fc region of IgG on its surface. By coating P815 targets with OKT3 (an anti-human CD3 monoclonal antibody) binding of the target cell to the effector T cell is accomplished by virtue of CD3 expression regardless of the T cell specificity. Thus, the killing of OKT3-coated P815 targets gives a indication of the cytolytic competence of the effector cell independent of its specificity. EM-2 and K562 are CML-derived cell lines, while Daudi is a B cell line and Jurkat a T cell line. All of these targets require recognition by the effector cells in order to be killed. FIGS. 6b–f show that the TcRγδ+ T cells expanded by the method of Example 6 were cytolytically competent and in addition, were able to recognize and kill both CML and non-CML derived target cells.

A portion of the TcRγδ+ T cells were cryopreserved in liquid nitrogen at a concentration of $2 \times 10^7$ cells/ml in HCBM-2 containing 10% autologous P and 10% dimethyl sulphoxide (DMSO). After thawing, approximately 71% of the frozen cells were recovered in a viable state, and the overall viability of the thawed cells was 90%. Approximately 70% of the thawed cells were TcRγδ+ and >70% of these were Vδ1+. A calcein-release assay using the thawed cells as effectors demonstrated that they maintained their cytolytic activity following cryopreservation and thawing, however this activity was reduced by a small extent for some of the target cell lines tested (FIGS. 6g–k). These results demonstrate that the TcRγδ+ T cells can be cryopreserved for use at a later date.

Example 7

TeABd33d: Con A/IL-2/IL-4/P->IL-2/IL-4/P=>TcRγδ+ T cells

LDMNC were isolated from the peripheral blood of a patient with chronic myelogenous leukemia (CML) as described in Example 1, and were enriched for TeABd as described in Example 2. The starting volume of whole blood was 43 ml. The starting number of LDMNC was $8.6 \times 10^7$ and the yield of TeABd was $2.5 \times 10^7$ representing 29% of the starting LDMNC. This yield was extremely high compared to that obtained from normal adult peripheral blood LDMNC (n=3, average LDMNC=$5.2 \times 10^7$, average TeABd= $3.4 \times 10^5$=<1%). Subsequent flow cytometry analysis of the CML patient-derived TeABd revealed a major non-T cell population of CD33+ myeloid progenitors representing about 78% of the CML-TeABd. To remove this subset of cells prior to culture for TcRγδ+ T cells, an anti-CD33 antibody was added to the TeABd cocktail in subsequent experiments involving CML patient cells. The resulting antibody cocktail, TeABd33d, contained antibodies specific for CD14, CD16, CD19, CD33, CD56 and glycophorin A.

Figure 7A:
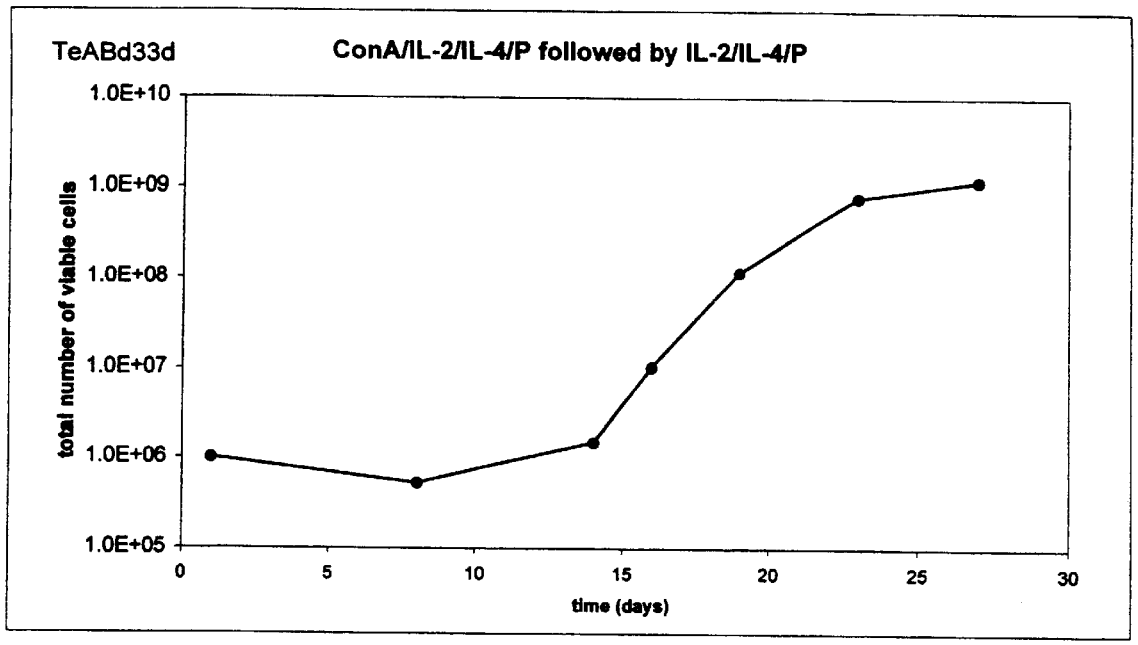
FIG. 7a is a graph showing the total viable cells over time during culture of T cell-enriched/TcRαβ-depleted/CD33-depleted cells derived from a CML patient cultured with conA/IL-2/IL-4/P followed by sub-culture with IL-2/IL-4/P.

In a subsequent experiment, LDMNC were isolated from the peripheral blood of a (different) CML patient as described in Example 1 and were enriched for TeABd33d as described in Example 2 using the modified antibody cocktail described above. The starting volume of whole blood was 40 ml. The starting number of LDMNC was $8.65 \times 10^7$ and the yield of TeABd33d was $1.3 \times 10^6$ (1.5%). The TeABd33d were expanded as described in Example 6. They were seeded into culture at a density of $1 \times 10^5$ cells/ml in HCBM-2 containing 1 ug/ml concanavalin A+10 ng/ml IL-2+10 ng/ml IL-4+5% P. They were expanded in the presence of concanavalin A+IL-2+IL-4+P to a total volume of 5 ml over a period of 14 days, at which point they were pelleted and washed by centrifugation and subsequently sub-cultured in HCBM-2 containing 10 ng/ml IL-2+10 ng/ml IL-4+5% P. The cells were expanded to a total culture volume of 1600 ml over the next 13 days (the total culture duration was 27 days), at which point the cell yield was $1.2 \times 10^9$. Although the cells were still expanding, the cells were harvested and used at this point. A graph of the growth kinetics is shown in FIG. 7a.

Flow cytometry analysis demonstrated that 72% of the cells were TcRγδ+ and most of these (>60%) were Vδ1+, while 33% were Vδ2+. Again, less than 3% of the cells expressed CD16 indicating that NK cells were not expanded in this culture.

Figure 7B:
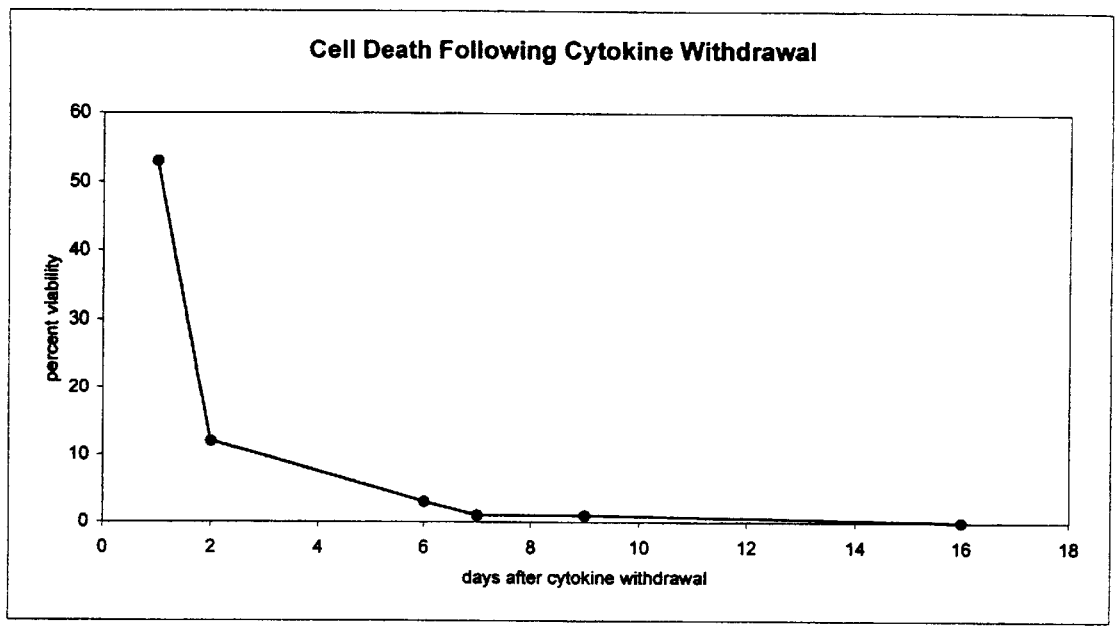
FIG. 7b is a graph showing percent viability versus time following cytokine withdrawal.
Figure 7C:
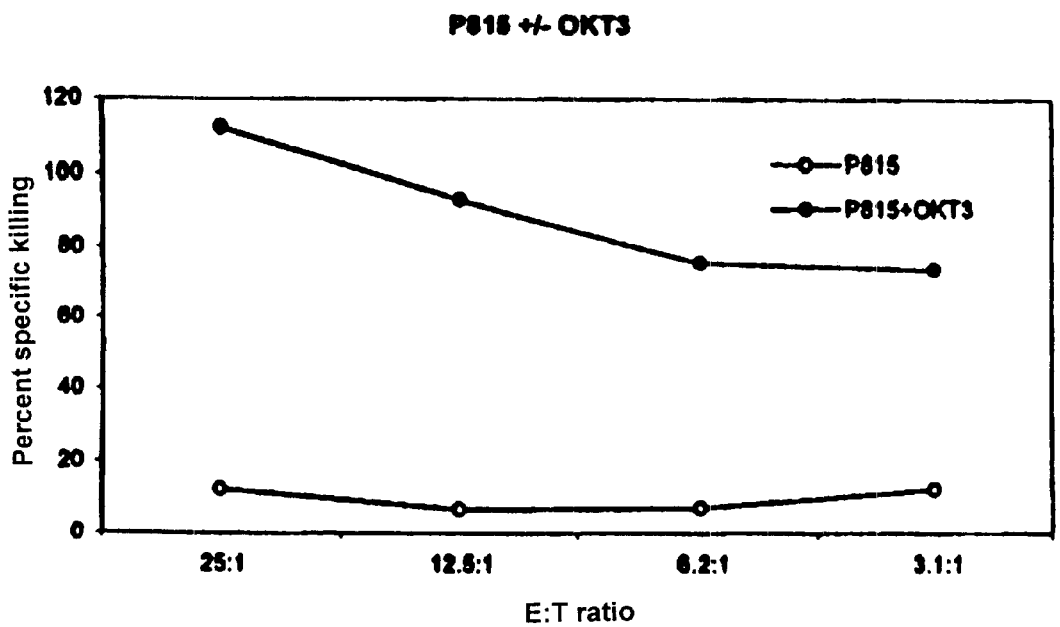
FIGS. 7c–g are graphs showing the percentage killing of various targets by TcRγδ+ effectors at various effector:target ratios.
Figure 7D:
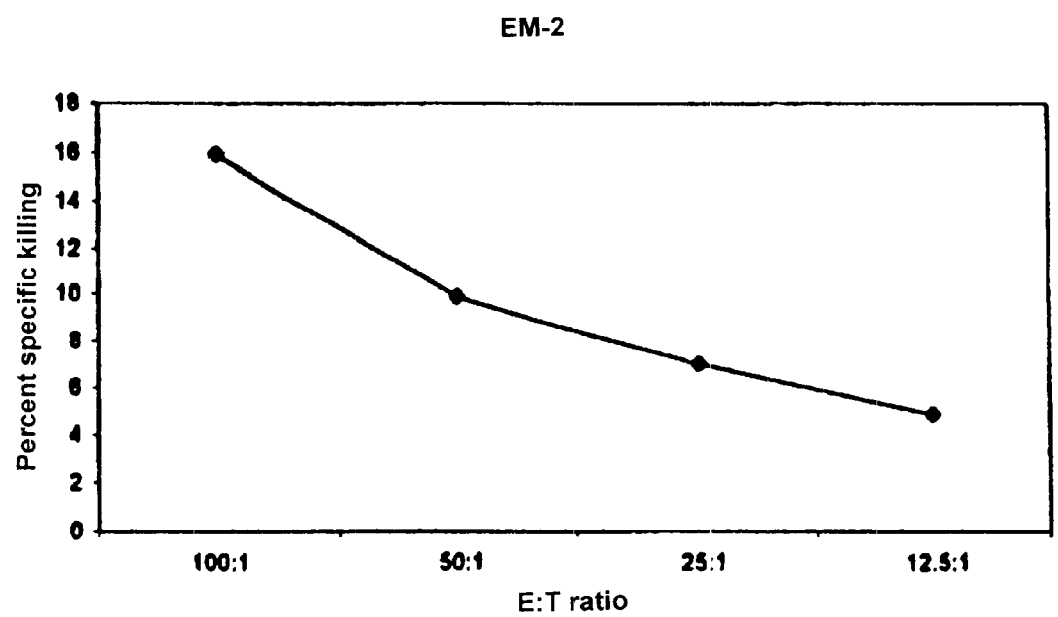
Figure 7E:
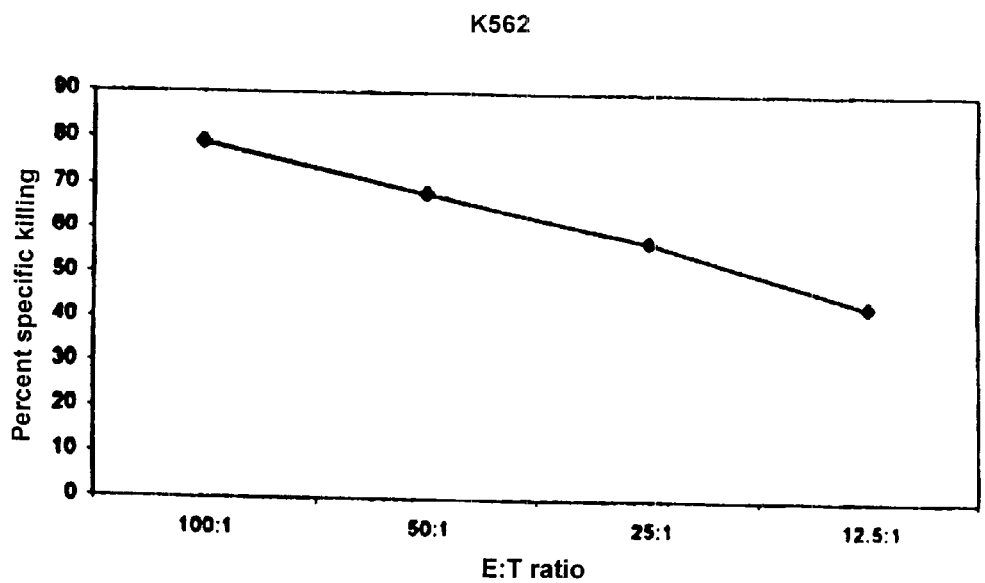
Figure 7F:
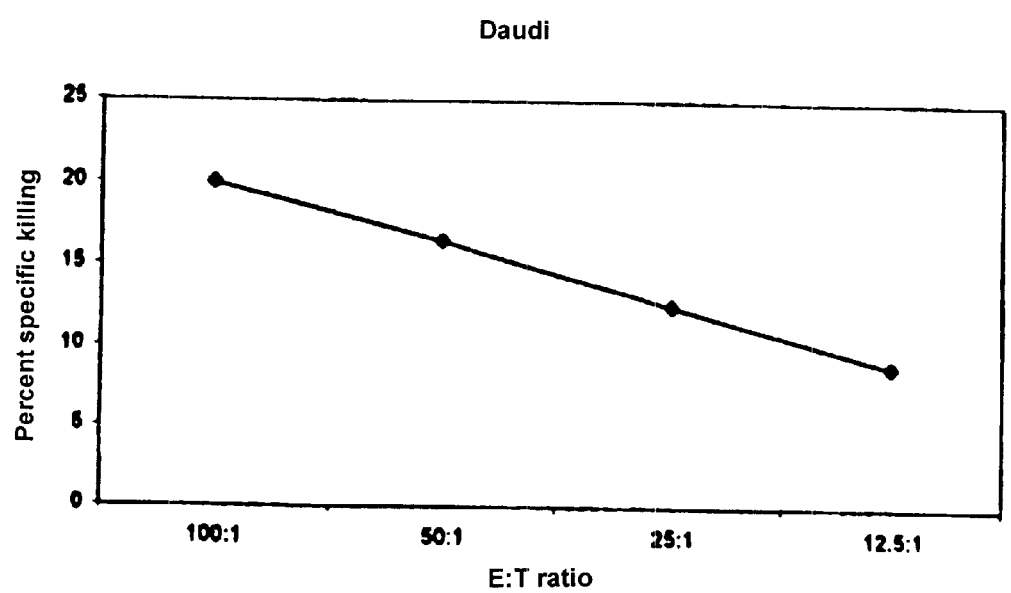
Figure 7G:
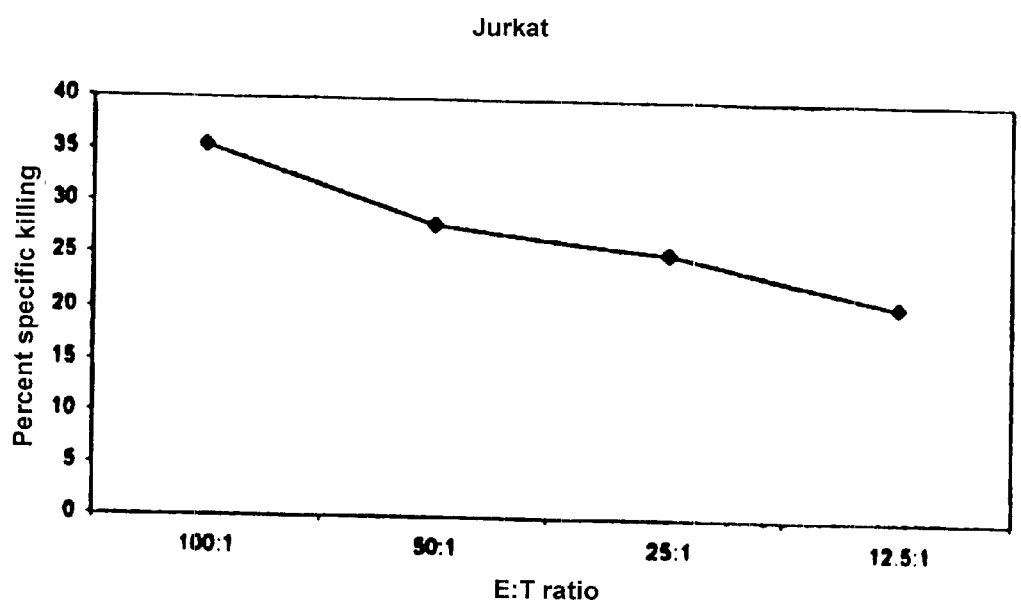
Figure 7H:
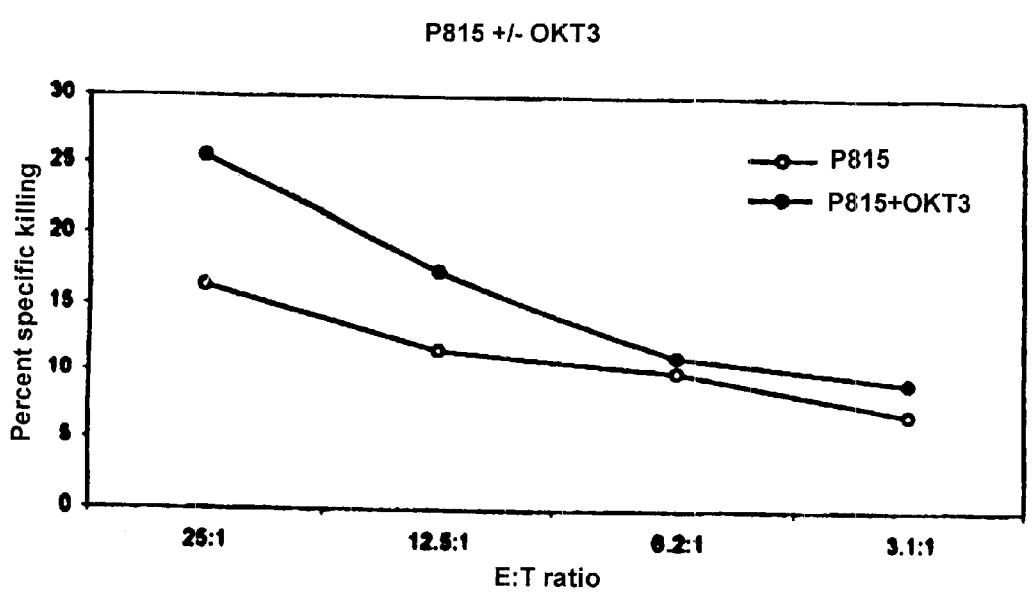
FIGS. 7h–l are graphs showing the percentage killing of various targets by TcRγδ+ effectors at various effector:target ratios after cryopreservation of the effectors.
Figure 7I:
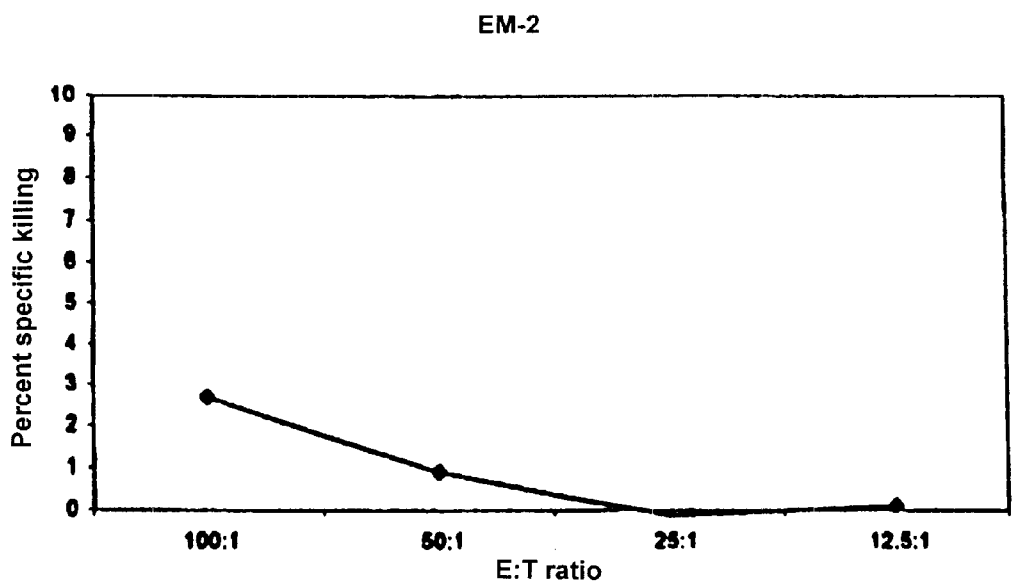
Figure 7J:
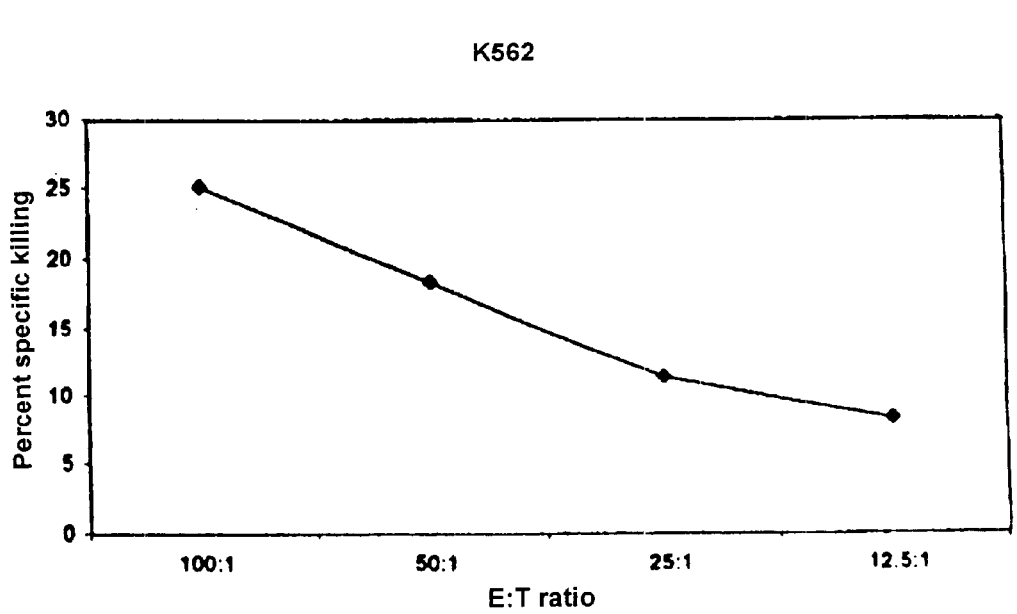
Figure 7K:
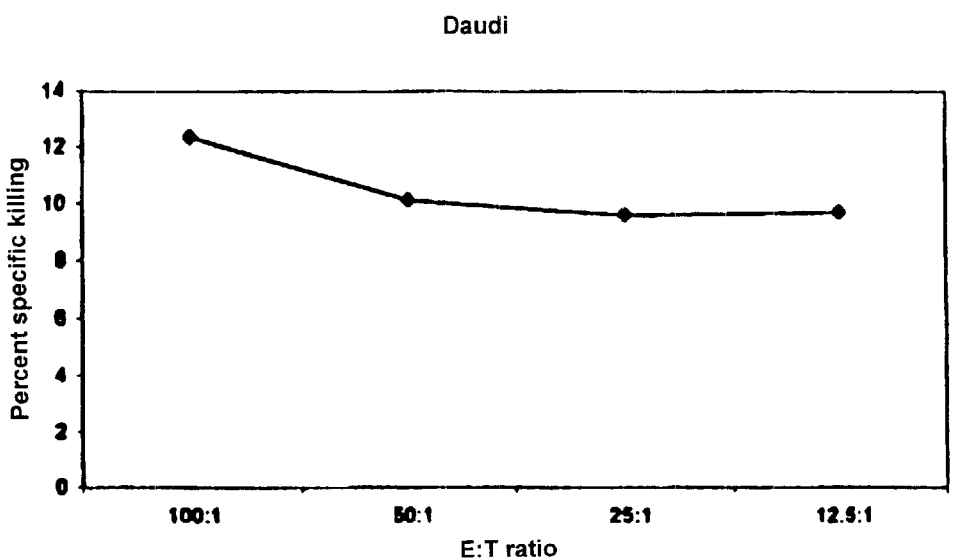
Figure 7L:
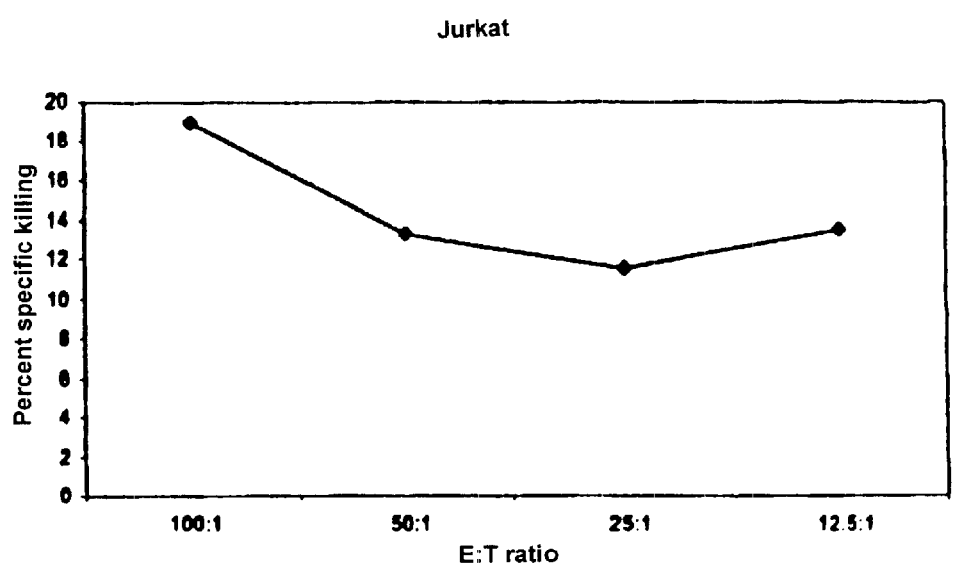

Cytogenetic analysis using standard G-banding techniques demonstrated that the expanded cells were non-leukemic with no clonal cytogenetic abnormalities detected including the Philadelphia chromosome which is the hallmark of CML. Subsequent culture of the cells in HCBM-2+5% P in the absence of IL-2 and IL-4 resulted in cell death, indicating that cell expansion is cytokine-dependent and indicating that the cultured cells were not transformed by the culture procedure (FIG. 7b).

The expanded cells were examined for the presence of concanavalin A bound to their surface. They were treated with rabbit anti-concanavalin A IgG antibody (RaConA) or with an equivalent amount of normal rabbit IgG. They were subsequently washed and stained with FITC-goat anti-rabbit IgG (NRIgG) and analyzed by flow cytometry. As a positive control LDMNC freshly cultured in concanavalin A+IL-2+IL-4+P (K) were similarly stained. The mean fluorescence intensity (MFI) of the positive control cells (K) stained with rabbit anti-concanavalin A antibody was far greater than the MFI obtained when the same cells were stained with normal rabbit IgG (Table 1) indicating the presence of concanavalin A on the cell surface. By contrast, the MFI of the TcR$\gamma\delta^+$ T cells was similar for both rabbit anti-concanavalin A antibody and normal rabbit IgG. These data indicate that the sub-culture of the cells in IL-2+IL-4+P (in the absence of concanavalin A) resulted in the elimination of detectable concanavalin A from the cultured cells most probably through internalization and catabolism or by shedding from the cell surface.

Cytotoxic activity of the CML patient-derived TcR$\gamma\delta^+$ T cells was confirmed using the calcein-release assay described in Example 6 (FIGS. 7c–g).

The CML patient-derived TcR$\gamma\delta^+$ T cells were cryopreserved in liquid nitrogen at a concentration of $4.4\times10^7$ cells/ml in HCBM-2 containing 10% autologous P and 10% DMSO. The recovery of viable cells after thawing was 76% and the overall viability of the thawed cells was 84%. Cytotoxic activity was maintained, but slightly reduced (FIGS. 7h–l).

These results verify that therapeutically useful numbers of functionally cytotoxic TcR$\gamma\delta^+$ T cells can be expanded ex vivo from a relatively small sample of peripheral blood taken from a CML patient. Further, these cells are non-leukemic and non-transformed, lack detectable surface concanavalin A and may be cryopreserved for use at a later time.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Absence of Con A on the Surface of Cultured TcR$\gamma\delta$+ T Cells

| HB1015C1: | LDMNC → TeABd33d → conA + IL-2 + IL-4 + P → IL-2 + IL-4 + P |  |  |
|---|---|---|---|
| K: | LDMNC → conA + IL-2 + IL-4 + P (positive control) |  |  |
|  | MFI |  | MFI Ratio*(RaConA) |
|  | RaConA | NRIgG | (NRIgG) |
| HB1015C1 | 0.726 | 0.865 | 0.84 |
| K | 5.76 | 1.32 | 4.36 |

*A ratio of ≦1 indicates that staining with rabbit anti-con A antibody (RaConA) is less than background staining with normal rabbit IgG (NRIgG).

These results demonstrate that con A is not detectable on the surface of the Cultured TcR$\gamma\delta^+$ T cells.

Full Citations for References Referred to in the Specification

Bensussan, A., Lagabrielle, J. F. Castaigne, S., Boisson, N., Miclea, J. M., Benbunan, M., Degos, L. Human CD3 gamma delta+activated lymphocytes exhibit killer activity in vitro against autologous leukemia cells. Nouv Rev Fr Hematol 31:129, 1989.

Boismenu, R., Havran, W. L. An innate view of $\gamma\delta$ T cells. Curr Op Immunol 9:57, 1997.

Bukowski, J. F., Morita, C. T., Brenner, M. B. Recognition and destruction of virus-infected cells by human $\gamma\delta$CTL. J. Immunol 153:5133, 1994.

Choudhary, A., Davodeau, F., Moreau, A., Peyrat, M. A., Bonneville, M., Jotereau, F. Selective lysis of autologous tumor cells by recurrent $\gamma\delta$ tumor-infiltrating lymphocytes from renal carcinoma. J Immunol 154:3932, 1995.

Constant, P., Davodeau, F., Peyrat, M., Poquet, Y., Puzo, G., Bonneville, M. and Fournie, J. Stimulation of human $\gamma\delta$ T cells by nonpeptidic mycobacterial ligands. Science 264:267, 1994.

Elloso, M. M., Van der Heyde, H. C., Troutt, A., Manning, D. D. and Weidanz, W. P. Human gamma delta T cell subset-proliferative response to malarial antigen in vitro depends on CD4$^+$ T cells or cytokines that signal through components of the IL-2R. J. Immunol. 157:2096, 1996.

Garcia, V. E., Jullien, D., Song, M., Uyemura, K., Shuai, K, Morita, C. T. and Modlin, R. L. IL-15 enhances the response of human gamma delta T cells to non-peptide microbial antigens. J. Immunol. 160:4322, 1998.

Jahn, B., Bergmann, L., Weidmann, E., Brieger, J., Fenchel, K., Schwulera, U., Hoelzer, D., Mitrou, P. S. Bone marrow-derived T-cell clones obtained from untreated acute myeolocytic leukemia exhibit blast directed autologous cytotoxicity. Leuk Res 19:73, 1995.

Kaur, I., Voss, S. D., Gupta, R. S., Schell, K., Fisch, P. and Sondel, P. M. Human peripheral $\gamma\delta$ T cells recognize hsp60 molecules on Daudi Burkitt's lymphoma cells. J. Immunol. 150:2046, 1993.

Kitayama, J., Atomi, Y., Nagawa, H., Kuroda, A., Mutoh, T., Minami, M., Juji, T. Functional analysis of TCR$\gamma\delta^+$ T cells in tumour-infiltrating lymphocytes (TIL) of human pancreatic cancer. Clin Exp Immunol 93:442, 1993.

Lamb, L. S., Henslee-Downey, P. J., Parrish, R. S., Godder, K., Thompson, J., Lee, C., Gee, A. P. Increased frequency of TCR gamma delta+T cells in disease-free survivors following T cell-depleted, partially mismatched, related donor bone marrow transplantation for leukemia. J Hematother 5:503, 1996.

Lang, F., Peyrat, M. A., Constant, P., Davodeau, F., David-Ameline, J., Poquet, Y., Vie, H., Foumie, J. J., Bonneville, M. J Immunol 154:5986, 1995.

Orsini, D. L. M., Res, P. C. M., Van Laar, J. M., Muller, L. M., Soprano, A. E. L., Kooy, Y. M. C., Tak, P. P. and Koning, F. A subset of V$\delta$1$^+$ T cells proliferates in response to Epstein-Barr virus-transformed B cell lines in vitro. Scand. J. Immunol. 38:335, 1993.

Penninger, J., Wen, T., Timms, E., Potter, J., Wallace, V. A., Matsuyama, T., Ferrick, D., Sydora, B., Kronenberg, M. Mak, T. W. Spontaneous resistance to acute T-cell leukaemias in TCR$\delta$1.1J$\gamma$4C$\gamma$4 transgenic mice. Nature 375:241, 1995.

Salerno, A. and Dieli, F. Role of $\gamma\delta$ T lymphocytes in immune response in humans and mice. Crit. Rev. Immunol. 18:327, 1998.

Skea, D., Chang, N., Hedge, R., Dabek, B., Wong, T., Wettlaufer, B. and Bell, D. Large ex vivo expansion of human umbilical cord blood CD4+ and CD8+ T cells. J. Hematotherapy 8:129, 1999.

Skea, D., Hedge, R., Dabek, B., Wettlaufer, B., Wong, T. and Bell, D. The selective expansion of functional T cell subsets. J. Hematotherapy and Stem Cell Research 8:525, 1999.

Suzuki, Y., Fujimiya, Y., Ohno, T., Katakura, R. and Yoshimoto, T. Enhancing effect of tumor necrosis factor (TNF)-α, but not IFN-γ, on the tumor-specific cytotoxicity of γδT cells from glioblastoma patients. Cancer Lett. 140:161, 1999.

Wallace, M., Malkovsky, M., Carding, S. R. Gamma/delta T lymphocytes in viral infections. J. Leuk Biol 58:277, 1995.

Yamaguchi, T., Fujimiya, Y., Suzuki, Y., Katakura, R. and Ebina, T. A simple method for the propagation and purification of γδT cells from the peripheral blood of glioblastoma patients using solid-phase anti-CD3 antibody and soluble IL-2. J. Immunol. Meth. 205:19, 1997.

Yu, S., He, W., Chen, J., Zhang, F. and Ba, D. Expansion and immunological study of human tumor infiltrating gamma/delta T lymphocytes in vitro. Int. Arch. Allergy Immunol. 119:31, 1999.

Zocchi, M. R., Ferrarini, M., Rugarli, C. Selective lysis of the autologous tumor by δTCS1+γδ+tumor-infiltrating lymphocytes from human lung carcinomas. Eur J Immunol 20:2685, 1990.

We claim:

1. A method for expanding TcRγδ+ T cells in a starting sample comprising:
   (1) culturing cells in the starting sample in a first culture medium comprising (a) a T cell mitogen, (b) interleukin-2 and (c) interleukin-4; and
   (2) culturing the cells obtained in step (1) in a second culture medium comprising (i) interleukin-2 and (ii) interleukin-4 to expand TcRγδ+ T cells, wherein said second culture medium does not contain a T cell mitogen.

2. A method for expanding TcRγδ+ T cells in a starting sample comprising:
   (1) culturing cells in the starting sample in a first culture medium comprising a conditioned medium prepared by stimulating umbilical cord blood cells with mezerein and concanavalin A; and
   (2) culturing the cells obtained in step (1) in a second culture medium comprising (i) interleukin-2 and (ii) interleukin-4 to expand TcRγδ+ T cells, wherein said second culture medium does not contain a T cell mitogen.

3. A method according to claim 1 wherein the first and second culture media contain serum or plasma.

4. A method according to claim 1 wherein prior to step (1) the cells in the starting sample are enriched for T cells.

5. A method according to claim 1 wherein prior to step (1) the cells in the starting sample are enriched for CD4+ cells.

6. A method according to claim 1 wherein prior to step (1) the cells in the starting sample are depleted of CD14+, CD16+, CD19+, CD56+ and glycophorin A+ cells.

7. A method according to claim 1 wherein prior to step (1) the cells in the starting sample are depleted of TcRαβ+ T cells.

8. A method according claim 1 wherein prior to step (1) the cells in the starting sample are depleted of non-TcRγδ+ T cells.

9. A method according to claim 1 wherein the starting sample is selected from peripheral blood, bone marrow, lymphoid tissue, epithelia, thymus, liver, spleen, cancerous tissue, infected tissue, lymph node tissue or fractions thereof.

10. A method according to claim 9 wherein the starting sample is human peripheral blood or a fraction thereof.

11. A method according to claim 1 wherein the starting sample is low density mononuclear cells.

12. A method according to claim 1 wherein in the first culture medium the T cell mitogen is present in an amount from about 0.01 to about 100 μg/ml; the IL-2 is present in an amount from about 0.1 to about 1000 ng/ml and the IL-4 is present in an amount from about 0.1 to about 1000 ng/ml.

13. A method according to claim 1 wherein in the first culture medium the T cell mitogen is present in an amount from about 0.1 to about 50 μg/ml; the IL-2 is present in an amount from about 1 to about 100 ng/ml and the IL-4 is present in an amount from about 1 to about 100 ng/ml.

14. A method according to claim 1 wherein in the first culture medium the T cell mitogen is present in an amount from about 0.5 to about 10 μg/ml; the IL-2 is present in an amount from about 2 to about 50 ng/ml and the IL-4 is present in an amount from about 2 to about 50 ng/ml.

15. A method according to claim 1 wherein the first culture medium comprises 1 μg/mL of a T cell mitogen; 10 ng/mL IL-2 and 10 ng/mL IL-4.

16. A method according to claim 1 wherein the T cell mitogen is concanavalin A.

17. A method according to claim 3 wherein the serum or plasma is present in an amount from about 1 to about 25% by volume.

18. A method according to claim 3 wherein the serum or plasma is present in an amount from about 2 to about 10% by volume.

19. A method according to claim 3 wherein the serum or plasma is present in an amount from about 2.5 to about 10% by volume.

20. A method according to claim 3 wherein the serum or plasma is present in an amount of about 5% by volume.

21. A method according to claim 1 wherein in the second culture medium the IL-2 is present in an amount from about 0.1 to about 1000 ng/ml and the IL-4 is present in an amount from about 0.1 to about 1000 ng/ml.

22. A method according to claim 1 wherein in the second culture medium the IL-2 is present in an amount from about 1 to about 100 ng/ml and the IL-4 is present in an amount from about 1 to about 100 ng/ml.

23. A method according claim 1 wherein in the second culture medium the IL-2 is present in an amount from about 2 to about 50 ng/ml and the IL-4 is present in an amount from about 2 to about 50 ng/ml.

24. A method according claim 1 wherein the second culture medium comprises 10 ng/mL IL-2 and 10 ng/mL IL-4.

25. A method according to claim 2 wherein the conditioned medium is present in an amount from about 1 to about 25%.

26. A method according to claim 2 wherein the conditioned medium is present in an amount from about 2 to about 20%.

27. A method according to claim 2 wherein the conditioned medium is present in an amount from about 2.5 to about 10%.

28. A method according to claim 2 wherein the conditioned medium is present in an amount from about 5%.

29. A method for obtaining TcRγδ+ T cells from a sample from a patient with chronic myelogenous leukemia comprising:
   (1) obtaining low density mononuclear cells (LDMNC) from the sample;
   (2) depleting the cells obtained in step (1) of CD33+ cells;

(3) culturing the cells obtained in step (2) in a first culture medium comprising (a) a T cell mitogen, (b) interleukin-2 and (c) interleukin-4; and
(4) culturing the cells obtained in step (3) in a second culture medium comprising (i) interleukin-2 and (ii) interleukin-4 to expand TcRγδ$^+$ T cells, wherein said second culture medium does not contain a T cell mitogen.

30. A method according to claim 29 wherein step (2) additionally comprises depleting the cells of CD14$^+$, CD16$^+$, CD19$^+$, CD56$^+$ and glycophorin A$^+$ cells.

31. A method according to claim 29 wherein step (2) additionally comprises depleting the cells of TcRαβ$^+$ T cells.

* * * * *